(12) United States Patent
Pandey et al.

(10) Patent No.: US 7,501,509 B2
(45) Date of Patent: Mar. 10, 2009

(54) WATER SOLUBLE TETRAPYROLLIC PHOTOSENSITIZERS FOR PHOTODYNAMIC THERAPY

(75) Inventors: Ravindra K. Pandey, Williamsville, NY (US); Amy Gryshuk, Pleasanton, CA (US); Lalit Goswami, Amherst, NY (US); William Potter, Grand Island, NY (US); Allan Oseroff, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 11/452,511

(22) Filed: Jun. 14, 2006

(65) Prior Publication Data

US 2007/0149497 A1 Jun. 28, 2007

Related U.S. Application Data

(63) Continuation-in-part of application No. 10/607,922, filed on Jun. 27, 2003, now Pat. No. 7,166,719.

(60) Provisional application No. 60/392,473, filed on Jun. 27, 2002.

(51) Int. Cl.
*C07B 47/00* (2006.01)
*C09D 48/22* (2006.01)

(52) U.S. Cl. ............ 540/145; 424/9.362; 424/9.6; 534/14

(58) Field of Classification Search ........ 540/140, 540/145; 534/14; 514/185, 410; 424/9.362, 424/9.6
See application file for complete search history.

(56) References Cited

U.S. PATENT DOCUMENTS

| | | | |
|---|---|---|---|
| 3,710,795 A | 1/1973 | Higuchi et al. | 128/260 |
| 3,817,837 A | 6/1974 | Rubenstein et al. | 195/103.5 R |
| 3,927,193 A | 12/1975 | Hansen et al. | 424/1 |
| RE28,819 E | 5/1976 | Thompson | 424/243 |
| 4,044,126 A | 8/1977 | Cook et al. | 424/243 |
| 4,328,245 A | 5/1982 | Yu et al. | 424/305 |
| 4,331,647 A | 5/1982 | Goldenberg | 424/1 |
| 4,348,376 A | 9/1982 | Goldenberg | 424/1 |
| 4,358,603 A | 11/1982 | Yu | 560/2 |
| 4,361,544 A | 11/1982 | Goldenberg | 424/1 |
| 4,364,923 A | 12/1982 | Cook et al. | 424/46 |
| 4,374,925 A | 2/1983 | Litman et al. | 435/7 |
| 4,409,239 A | 10/1983 | Yu | 424/305 |
| 4,410,545 A | 10/1983 | Yu et al. | 424/305 |
| 4,414,209 A | 11/1983 | Cook et al. | 424/243 |
| 4,444,744 A | 4/1984 | Goldenberg | 424/1.1 |
| 4,468,457 A | 8/1984 | Goldenberg et al. | 435/69 |
| 4,474,893 A | 10/1984 | Reading | 436/547 |
| 4,479,895 A | 10/1984 | Auditore-Hargreaves | 260/112 B |
| 4,521,762 A | 6/1985 | Kapral | 340/347 |
| 4,522,811 A | 6/1985 | Eppstein et al. | 514/2 |
| 4,577,636 A | 3/1986 | Spears | 128/654 |
| 4,624,846 A | 11/1986 | Goldenberg | 424/1.1 |
| 4,649,151 A | 3/1987 | Dougherty et al. | 514/410 |
| 4,656,186 A | 4/1987 | Bommer et al. | 514/410 |
| 4,675,338 A | 6/1987 | Bommer et al. | 514/410 |
| 4,693,885 A | 9/1987 | Bommer et al. | 424/9.61 |

(Continued)

FOREIGN PATENT DOCUMENTS

EP 0120054 B1 3/1984

(Continued)

OTHER PUBLICATIONS

Smith et al., Bacteriochlorophylls c from Chloropseudomonas Ethylicum, Composition and NMR Studies of the Pheophorbides and Derivatives, Journal of the American Chemical Society, 1980, 2437-2448.*

(Continued)

*Primary Examiner*—Yvonne Eyler
*Assistant Examiner*—Chukwuma O Nwaonicha
(74) *Attorney, Agent, or Firm*—Michael L. Dunn

(57) ABSTRACT

A tetrapyrollic photosensitizer compound having at least one pendant $-CH_2CH_2CON(CH_2CON(CH_2COOH)_2)_2$ or $-N(CH_2COOH)_2$ group or esters thereof said tetrapyrollic compound being a chlorin, bacteriochlorin, porphyrin, pyropheophorbide, purpurinimide, or bacteriopurpurinimide. Desirably the compound has the formula:

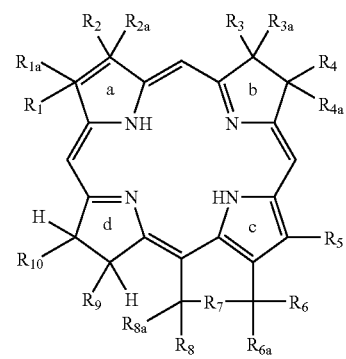

or a phamaceutically acceptable derivative thereof, wherein $R_1$-$R_8$ and $R_{10}$ are various substituents and $R_9$ is substituted or unsubstituted $-CH_2CH_2CON(CH_2CON(CH_2COOH)_2)_2$; or $-N(CH_2COOH)_2$. The invention also includes a method of treatment by photodynamic therapy by treatment with light after injecting the compound and a method of imaging by fluorescence after injection of the compound.

12 Claims, 5 Drawing Sheets

U.S. PATENT DOCUMENTS

| | | | |
|---|---|---|---|
| 4,753,958 A | 6/1988 | Weinstein et al. | 514/410 |
| 4,818,709 A | 4/1989 | Primus et al. | 436/518 |
| 4,861,876 A | 8/1989 | Kessel | 540/145 |
| 4,866,168 A | 9/1989 | Dougherty et al. | 540/145 |
| 4,878,891 A | 11/1989 | Judy et al. | 604/5 |
| 4,889,129 A | 12/1989 | Dougherty et al. | 128/664 |
| 4,916,221 A | 4/1990 | Kumadaki et al. | 540/145 |
| 4,925,736 A | 5/1990 | Shikowitz | 424/449 |
| 4,932,934 A | 6/1990 | Dougherty et al. | 604/21 |
| 4,935,498 A | 6/1990 | Sessler et al. | 534/15 |
| 4,946,778 A | 8/1990 | Ladner et al. | 435/69.6 |
| 4,957,481 A | 9/1990 | Gatenby | 604/20 |
| 4,968,715 A | 11/1990 | Dougherty et al. | 514/410 |
| 4,997,639 A | 3/1991 | Aizawa et al. | 424/9 |
| 5,002,962 A | 3/1991 | Pandey et al. | 514/410 |
| 5,004,811 A | 4/1991 | Bommer et al. | 540/145 |
| 5,015,463 A | 5/1991 | Dougherty et al. | 424/7.1 |
| 5,028,594 A | 7/1991 | Carson | 514/23 |
| 5,028,621 A | 7/1991 | Dougherty et al. | 514/410 |
| 5,033,252 A | 7/1991 | Carter | 53/425 |
| 5,041,078 A | 8/1991 | Matthes et al. | 604/4 |
| 5,051,415 A | 9/1991 | Moran et al. | 514/185 |
| 5,052,558 A | 10/1991 | Carter | 206/439 |
| 5,053,006 A | 10/1991 | Watson | 604/52 |
| 5,059,415 A | 10/1991 | Neuwelt | 424/9 |
| 5,062,431 A | 11/1991 | Potter | 128/665 |
| 5,066,274 A | 11/1991 | Bommer et al. | 604/20 |
| 5,066,291 A | 11/1991 | Stewart | 606/3 |
| 5,074,632 A | 12/1991 | Potter | 385/31 |
| 5,093,349 A | 3/1992 | Pandey et al. | 514/410 |
| 5,095,030 A | 3/1992 | Levy et al. | 514/410 |
| 5,111,821 A | 5/1992 | Potter | 128/654 |
| 5,145,863 A | 9/1992 | Dougherty et al. | 514/410 |
| 5,171,741 A | 12/1992 | Dougherty | 514/185 |
| 5,173,504 A | 12/1992 | Dougherty | 514/410 |
| 5,190,536 A | 3/1993 | Wood et al. | 606/16 |
| 5,190,966 A | 3/1993 | Dougherty et al. | 514/410 |
| 5,198,460 A | 3/1993 | Pandey et al. | 514/410 |
| 5,205,291 A | 4/1993 | Potter | 128/654 |
| 5,216,012 A | 6/1993 | Morgan et al. | 514/410 |
| 5,219,345 A | 6/1993 | Potter | 606/15 |
| 5,222,795 A | 6/1993 | Hed | 362/32 |
| 5,225,433 A | 7/1993 | Dougherty et al. | 514/410 |
| 5,257,970 A | 11/1993 | Dougherty | 604/20 |
| 5,263,925 A | 11/1993 | Gilmore, Jr. et al. | 604/4 |
| 5,298,018 A | 3/1994 | Narciso, Jr. | 604/21 |
| 5,308,861 A | 5/1994 | Aizawa et al. | 514/410 |
| 5,314,905 A | 5/1994 | Pandey et al. | 514/410 |
| 5,323,907 A | 6/1994 | Kalvelage | 206/531 |
| 5,330,741 A | 7/1994 | Smith et al. | 424/9 |
| 5,344,928 A | 9/1994 | Masuya et al. | 544/37 |
| 5,368,841 A | 11/1994 | Trauner et al. | 424/9 |
| 5,403,308 A | 4/1995 | Wood et al. | 606/17 |
| 5,418,130 A | 5/1995 | Platz et al. | 435/2 |
| 5,430,051 A | 7/1995 | Aizawa et al. | 514/410 |
| 5,441,531 A | 8/1995 | Zarate et al. | 607/90 |
| 5,459,159 A | 10/1995 | Pandey et al. | 514/410 |
| 5,482,698 A | 1/1996 | Griffiths | 424/141 |
| 5,484,803 A | 1/1996 | Richter | 514/410 |
| 5,496,308 A | 3/1996 | Brown et al. | 606/15 |
| 5,498,710 A * | 3/1996 | Pandey et al. | 540/145 |
| 5,500,009 A | 3/1996 | Mendes et al. | 607/88 |
| 5,503,637 A | 4/1996 | Kyricos et al. | 607/88 |
| 5,506,255 A | 4/1996 | Smith et al. | 514/410 |
| 5,514,669 A | 5/1996 | Selman | 514/63 |
| 5,525,338 A | 6/1996 | Goldenberg | 424/178.1 |
| 5,532,171 A | 7/1996 | Motsenbocker | 436/533 |
| 5,534,506 A | 7/1996 | Morgan et al. | 514/185 |
| 5,549,660 A | 8/1996 | Mendes et al. | 607/88 |
| 5,556,612 A | 9/1996 | Anderson et al. | 424/59 |
| 5,567,409 A | 10/1996 | Aizawa et al. | 424/9.363 |
| 5,571,152 A | 11/1996 | Chen et al. | 607/92 |
| 5,580,896 A | 12/1996 | Horwell et al. | 514/419 |
| 5,591,847 A * | 1/1997 | Pandey et al. | 540/472 |
| 5,594,136 A | 1/1997 | Sessler et al. | 540/472 |
| 5,599,923 A | 2/1997 | Sessler et al. | 540/145 |
| 5,622,983 A | 4/1997 | Horwell et al. | 514/419 |
| 5,624,798 A | 4/1997 | Yamamoto et al. | 435/6 |
| 5,631,281 A | 5/1997 | Horwell et al. | 514/419 |
| 5,648,485 A | 7/1997 | Dolphin et al. | 540/474 |
| 5,665,328 A | 9/1997 | Horan et al. | 424/1.17 |
| 5,671,317 A | 9/1997 | Weishaupt et al. | 385/137 |
| 5,688,486 A | 11/1997 | Watson et al. | 424/1.65 |
| 5,697,902 A | 12/1997 | Goldenberg | 604/49 |
| 5,698,405 A | 12/1997 | Goldenberg | 435/7.5 |
| 5,702,432 A | 12/1997 | Chen et al. | 607/88 |
| 5,703,230 A | 12/1997 | Boyle et al. | 540/145 |
| 5,705,518 A | 1/1998 | Richter et al. | 514/410 |
| 5,709,874 A | 1/1998 | Hanson et al. | 424/423 |
| 5,715,837 A | 2/1998 | Chen | 128/899 |
| 5,716,595 A | 2/1998 | Goldenberg | 414/1.49 |
| 5,736,563 A | 4/1998 | Richter | 514/410 |
| 5,741,316 A | 4/1998 | Chen et al. | 607/61 |
| 5,759,542 A | 6/1998 | Gurewich | 424/94.64 |
| 5,766,234 A | 6/1998 | Chen et al. | 607/92 |
| 5,770,619 A | 6/1998 | Richter et al. | 514/410 |
| 5,770,730 A * | 6/1998 | Pandey et al. | 23/302 T |
| 5,773,977 A | 6/1998 | Dougherty | 324/429 |
| 5,776,093 A | 7/1998 | Goldenberg | 604/20 |
| 5,776,094 A | 7/1998 | Goldenberg | 604/20 |
| 5,776,095 A | 7/1998 | Goldenberg | 604/20 |
| 5,782,896 A | 7/1998 | Chen et al. | 607/88 |
| 5,800,478 A | 9/1998 | Chen et al. | 607/88 |
| 5,814,008 A | 9/1998 | Chen et al. | 604/21 |
| 5,824,080 A | 10/1998 | Lamuraglia | 623/11 |
| 5,827,186 A | 10/1998 | Chen et al. | 600/407 |
| 5,829,448 A | 11/1998 | Fisher et al. | 128/898 |
| 5,831,088 A | 11/1998 | Dolphin et al. | 540/474 |
| 5,832,931 A | 11/1998 | Wachter et al. | 128/898 |
| 5,840,674 A | 11/1998 | Yatvin et al. | 514/2 |
| 5,851,225 A | 12/1998 | Lawandy | 607/88 |
| 5,860,957 A | 1/1999 | Jacobsen et al. | 604/156 |
| 5,864,035 A | 1/1999 | Pandey et al. | 540/472 |
| 5,865,840 A | 2/1999 | Chen | 607/92 |
| 5,876,427 A | 3/1999 | Chen et al. | 607/88 |
| 5,885,557 A | 3/1999 | Lentini | 424/59 |
| 5,886,173 A | 3/1999 | Hemmi et al. | 540/472 |
| 5,900,252 A | 5/1999 | Calanchi et al. | 424/459 |
| 5,913,884 A | 6/1999 | Trauner et al. | 607/88 |
| 5,921,244 A | 7/1999 | Chen et al. | 128/897 |
| 5,942,534 A | 8/1999 | Trauner et al. | 514/410 |
| 5,944,748 A | 8/1999 | Mager et al. | 607/88 |
| 5,945,762 A | 8/1999 | Chen et al. | 310/171 |
| 5,948,433 A | 9/1999 | Burton et al. | 424/448 |
| 5,952,366 A * | 9/1999 | Pandey et al. | 514/410 |
| 5,957,960 A | 9/1999 | Chen et al. | 607/92 |
| 5,972,366 A | 10/1999 | Haynes et al. | 424/422 |
| 5,976,535 A | 11/1999 | Fritzberg et al. | 424/182.1 |
| 5,983,134 A | 11/1999 | Ostrow | 604/20 |
| 5,985,307 A | 11/1999 | Hanson et al. | 424/423 |
| 5,985,317 A | 11/1999 | Venkateshwaran et al. | 424/449 |
| 5,997,569 A | 12/1999 | Chen et al. | 607/88 |
| 5,997,842 A | 12/1999 | Chen | 424/1.29 |
| 5,998,597 A | 12/1999 | Fisher et al. | 536/23.1 |
| 6,004,534 A | 12/1999 | Langer et al. | 424/9.321 |
| 6,010,715 A | 1/2000 | Wick et al. | 424/448 |
| 6,015,897 A | 1/2000 | Theodore et al. | 540/474 |
| 6,022,961 A | 2/2000 | Yamamoto et al. | 536/24.3 |
| 6,024,975 A | 2/2000 | D'Angelo et al. | 424/449 |
| 6,028,099 A | 2/2000 | de Juan, Jr. | 514/434 |
| 6,036,941 A | 3/2000 | Bottiroli et al. | 424/9.6 |
| 6,039,975 A | 3/2000 | Shah et al. | 424/473 |
| 6,048,359 A | 4/2000 | Biel | 607/92 |
| 6,048,736 A | 4/2000 | Kosak | 436/536 |

| | | | |
|---|---|---|---|
| 6,051,207 A | 4/2000 | Klaveness et al. ............. 424/9.1 |
| 6,051,702 A | 4/2000 | Bird et al. .................... 540/122 |
| 6,060,082 A | 5/2000 | Chen et al. .................... 424/450 |
| 6,063,108 A | 5/2000 | Salansky et al. ............... 607/89 |
| 6,063,777 A | 5/2000 | Hikida et al. ................ 514/183 |
| 6,071,495 A | 6/2000 | Unger et al. ................ 424/9.51 |
| 6,080,160 A | 6/2000 | Chen et al. .................... 606/72 |
| 6,084,717 A | 7/2000 | Wood et al. ................. 359/629 |
| 6,090,788 A | 7/2000 | Lurie .......................... 514/23 |
| 6,092,531 A | 7/2000 | Chen et al. .................... 128/899 |
| 6,096,066 A | 8/2000 | Chen et al. .................... 607/88 |
| 6,096,289 A | 8/2000 | Goldenberg ............... 424/1.49 |
| 6,100,893 A | 8/2000 | Ensz et al. .................. 345/420 |
| 6,103,751 A * | 8/2000 | Pandey et al. ............... 514/410 |
| 6,107,466 A | 8/2000 | Hasan et al. ................. 530/351 |
| 6,117,862 A | 9/2000 | Margaron et al. ........... 514/410 |
| 6,120,751 A | 9/2000 | Unger ....................... 424/9.51 |
| 6,123,923 A | 9/2000 | Unger et al. ............... 424/9.52 |
| 6,124,342 A | 9/2000 | Okamoto et al. ............. 514/432 |
| 6,131,570 A | 10/2000 | Schuster et al. ........ 128/203.26 |
| 6,138,681 A | 10/2000 | Chen et al. .................. 128/899 |
| 6,139,865 A | 10/2000 | Friend et al. ................ 424/441 |
| 6,152,951 A | 11/2000 | Hashimoto et al. ............ 607/92 |
| 6,156,506 A | 12/2000 | Yamamoto et al. ............. 435/6 |
| 6,162,213 A | 12/2000 | Stewart ....................... 606/10 |
| 6,162,242 A | 12/2000 | Peyman ....................... 607/88 |
| 6,167,301 A | 12/2000 | Flower et al. ................. 604/20 |
| 6,176,842 B1 | 1/2001 | Tachibana et al. ............. 604/22 |
| 6,187,030 B1 | 2/2001 | Gart et al. .................... 607/93 |
| 6,210,425 B1 | 4/2001 | Chen ........................... 607/88 |
| 6,217,869 B1 | 4/2001 | Meyer et al. ............... 424/178.1 |
| RE37,180 E | 5/2001 | Mori et al. .................. 514/410 |
| 6,232,295 B1 | 5/2001 | Kayyem et al. ............... 514/44 |
| 6,238,426 B1 | 5/2001 | Chen ........................... 607/88 |
| 6,242,477 B1 | 6/2001 | Okamoto et al. ............. 514/432 |
| 6,253,872 B1 | 7/2001 | Neumann ................... 181/210 |
| 6,256,533 B1 | 7/2001 | Yuzhakov et al. .............. 604/21 |
| 6,261,595 B1 | 7/2001 | Stanley et al. ............... 424/449 |
| 6,264,914 B1 | 7/2001 | Klaveness et al. ........... 424/1.65 |
| 6,267,983 B1 | 7/2001 | Fujii et al. .................. 424/448 |
| 6,268,120 B1 | 7/2001 | Platz et al. ..................... 435/2 |
| 6,271,359 B1 | 8/2001 | Norris et al. ................ 536/23.1 |
| 6,273,904 B1 | 8/2001 | Chen et al. .................... 607/88 |
| 6,274,552 B1 | 8/2001 | Tamarkin et al. ............. 514/12 |
| 6,281,611 B1 | 8/2001 | Chen et al. .................... 310/171 |
| 6,307,147 B1 | 10/2001 | Bird et al. ................... 136/263 |
| 6,316,652 B1 | 11/2001 | Steliou ........................ 556/42 |
| 6,319,273 B1 | 11/2001 | Chen et al. .................... 607/88 |
| 6,319,488 B1 | 11/2001 | Licha et al. .................. 424/9.6 |
| 6,331,175 B1 | 12/2001 | Goldenberg ................ 604/522 |
| 6,331,744 B1 | 12/2001 | Chen et al. .................... 310/171 |
| 6,344,050 B1 | 2/2002 | Chen ........................... 607/88 |
| 6,350,431 B1 | 2/2002 | Snow et al. .................. 424/9.6 |
| 6,387,350 B2 | 5/2002 | Goldenberg ................ 424/1.57 |
| 6,406,297 B1 | 6/2002 | Raymond et al. ............. 434/15 |
| 6,416,531 B2 | 7/2002 | Chen ........................... 607/89 |
| 6,454,789 B1 | 9/2002 | Chen et al. .................... 607/88 |
| 6,482,517 B1 | 11/2002 | Anderson ............... 428/402.24 |
| 6,489,314 B1 | 12/2002 | Ashley et al. ............... 514/183 |
| 6,495,585 B2 | 12/2002 | Bellnier et al. ............... 514/410 |
| 6,498,945 B1 | 12/2002 | Alfheim et al. .............. 600/407 |
| 6,500,816 B1 | 12/2002 | Ekimoto et al. ............. 514/185 |
| 6,511,971 B1 | 1/2003 | Gorun ........................ 514/183 |
| 6,514,995 B1 | 2/2003 | Zaleski et al. ............... 514/332 |
| 6,515,113 B2 | 2/2003 | Raymond et al. ............. 534/15 |
| 6,520,669 B1 | 2/2003 | Chen et al. ................... 362/545 |
| 6,524,552 B2 | 2/2003 | Klaveness et al. .......... 424/1.85 |
| 6,525,088 B1 | 2/2003 | Nagano et al. ............... 514/452 |
| 6,527,759 B1 | 3/2003 | Tachibana et al. ........... 604/500 |
| 6,534,040 B2 | 3/2003 | Pandey et al. ................ 424/362 |
| 6,540,980 B1 | 4/2003 | Blumenthal et al. ........ 424/9.34 |
| 6,554,853 B1 | 4/2003 | Chen ........................... 607/88 |
| 6,559,374 B2 | 5/2003 | Lindsey et al. .............. 136/263 |
| 6,566,517 B2 | 5/2003 | Miura et al. ................. 540/145 |
| 6,569,846 B1 | 5/2003 | Scherz et al. ................ 514/185 |
| 6,572,839 B2 | 6/2003 | Sugita et al. ................. 424/9.5 |
| 6,580,228 B1 | 6/2003 | Chen et al. ............... 315/185 R |
| 6,602,274 B1 | 8/2003 | Chen ........................... 607/88 |
| 6,624,187 B1 | 9/2003 | Pandey et al. ............... 514/410 |
| 6,657,351 B2 | 12/2003 | Chen et al. .................... 310/171 |
| 6,899,723 B2 | 5/2005 | Chen |
| 6,986,782 B2 | 1/2006 | Chen et al. |
| RE38,994 E | 2/2006 | Pandey et al. |
| 7,018,395 B2 | 3/2006 | Chen |
| RE39,094 E | 5/2006 | Pandey et al. |
| 7,053,210 B2 | 5/2006 | Pandey et al. |
| 2001/0022970 A1 | 9/2001 | Dees et al. ................. 424/178.1 |
| 2002/0033192 A1 | 3/2002 | Lindsey et al. .............. 136/263 |
| 2002/0049247 A1 | 4/2002 | Chen ........................... 514/410 |
| 2002/0087205 A1 | 7/2002 | Chen ........................... 607/88 |
| 2002/0127224 A1 | 9/2002 | Chen ......................... 424/130.1 |
| 2002/0127230 A1 | 9/2002 | Chen ......................... 424/178.1 |
| 2002/0128303 A1 | 9/2002 | Bellnier et al. .............. 514/410 |
| 2002/0198576 A1 | 12/2002 | Chen et al. .................... 607/88 |
| 2003/0018371 A1 | 1/2003 | Chen ........................... 607/88 |
| 2003/0030342 A1 | 2/2003 | Chen et al. .................... 310/102 |
| 2003/0109813 A1 | 6/2003 | Chen ........................... 601/2 |
| 2003/0114434 A1 | 6/2003 | Chen et al. .................. 514/185 |
| 2003/0167033 A1 | 9/2003 | Chen et al. ................... 604/20 |
| 2003/0208249 A1 | 11/2003 | Chen ........................... 607/88 |
| 2004/0044197 A1 | 3/2004 | Pandey et al. ............... 540/140 |
| 2004/0044198 A1 | 3/2004 | Pandey et al. ............... 540/145 |

FOREIGN PATENT DOCUMENTS

| | | |
|---|---|---|
| EP | 0161606 B1 | 11/1985 |
| EP | 02439929 B1 | 11/1987 |
| EP | 0423195 B1 | 4/1991 |
| EP | 0425566 B1 | 5/1991 |
| EP | 0450149 B1 | 10/1991 |
| EP | 0468997 B1 | 2/1992 |
| EP | 0510007 B1 | 10/1992 |
| EP | 0682956 B1 | 11/1995 |
| EP | 1110963 A2 | 6/2001 |
| EP | 1131100 B1 | 9/2001 |
| EP | 1146046 A2 | 10/2001 |
| EP | 1164136 A1 | 12/2001 |
| EP | 1238666 A2 | 9/2002 |
| EP | 1256586 A1 | 11/2002 |
| EP | 1334748 A1 | 8/2003 |
| JP | 4218002 | 7/1992 |
| JP | 6105921 | 4/1994 |
| JP | 2001335578 | 4/2001 |
| JP | 2002020389 | 1/2002 |
| JP | 2002325853 | 11/2002 |
| JP | 2003146989 | 5/2003 |
| WO | 8401382 A1 | 4/1984 |
| WO | 9000392 A1 | 1/1990 |
| WO | 9000895 A1 | 2/1990 |
| WO | 9012573 A1 | 11/1990 |
| WO | 9110474 A1 | 7/1991 |
| WO | 9313769 A1 | 7/1993 |
| WO | 9409851 A1 | 5/1994 |
| WO | 9505214 A1 | 2/1995 |
| WO | 9532206 A1 | 11/1995 |
| WO | 9637255 A1 | 11/1996 |
| WO | 9732520 A1 | 9/1997 |
| WO | 9732885 A1 | 9/1997 |
| WO | 9804317 A1 | 2/1998 |
| WO | 9806456 A1 | 2/1998 |
| WO | 9808565 A1 | 3/1998 |
| WO | 9814243 A1 | 4/1998 |
| WO | 9824371 A1 | 6/1998 |
| WO | 9824510 A1 | 6/1998 |
| WO | 9832491 A1 | 7/1998 |
| WO | 9832492 A1 | 7/1998 |

| | | |
|---|---|---|
| WO | 9832493 A1 | 7/1998 |
| WO | 9846130 A1 | 10/1998 |
| WO | 9850034 A1 | 11/1998 |
| WO | 9856302 A1 | 12/1998 |
| WO | 9918879 A1 | 4/1999 |
| WO | 9920346 A1 | 4/1999 |
| WO | 9939769 A1 | 8/1999 |
| WO | 9952565 A1 | 10/1999 |
| WO | 9958149 A1 | 11/1999 |
| WO | 9966988 A1 | 12/1999 |
| WO | 9967248 A1 | 12/1999 |
| WO | WO99/67248 | 12/1999 |
| WO | WO99/67249 | 12/1999 |
| WO | 0015296 A1 | 3/2000 |
| WO | 0036983 A1 | 6/2000 |
| WO | 0041725 A2 | 7/2000 |
| WO | 0041726 A3 | 7/2000 |
| WO | 0041727 A1 | 7/2000 |
| WO | 0041768 A1 | 7/2000 |
| WO | 00/61584 A1 | 10/2000 |
| WO | 0103770 A1 | 1/2001 |
| WO | 0105316 A1 | 1/2001 |
| WO | 0115694 A1 | 3/2001 |
| WO | 0143825 A1 | 6/2001 |
| WO | 0151087 A2 | 7/2001 |
| WO | 01/74398 A1 | 10/2001 |
| WO | 0178216 A1 | 10/2001 |
| WO | 0178458 A1 | 10/2001 |
| WO | 0198708 A1 | 12/2001 |
| WO | 0217690 A1 | 2/2002 |
| WO | 02/098882 A1 | 12/2002 |
| WO | 03029494 A1 | 4/2003 |
| WO | 03/050082 A2 | 6/2003 |
| WO | 03052793 A2 | 6/2003 |
| WO | WO03/052793 | 6/2003 |
| WO | 03056407 A2 | 7/2003 |
| WO | 03061696 A2 | 7/2003 |
| WO | WO03/061696 | 7/2003 |
| WO | 2004/002476 A2 | 1/2004 |
| WO | 2004/005289 A2 | 1/2004 |
| WO | WO2004/002476 | 1/2004 |
| WO | WO2004/002486 | 1/2004 |
| WO | WO2004/005289 | 1/2004 |

OTHER PUBLICATIONS

Li et al. Application for Ruppert's Reagent in Preparing Novel Perfluorinated Porphyrins, Chlorins and Bacteriochlorins, J. Chem. Soc., Perkin Trans. 1, 1999, 1785-1787.*

Bellnier et al., "Population pharmacokinetics of the photodynamic therapy agent 2-[1-hexyloxyethyl]-2-devinyl pyropheophorbide-a in cancer patients", *Cancer Res.*, 63(8):1806-1813 (2003).

Bellnier et al., "Design and construction of a light-delivery system for photodynamic therapy", *Med. Phys.*, 26(8):1552-1558 (1999).

Bellnier et al., "The time course of cutaneous porphyrin photosensitization in the murine ear", *Photochemistry and Photobiology*, 49(3):369-372 (1989).

Bellnier et al., "Murine pharmacokinetics and antitumor efficacy of the photodynamic sensitizer 2-[1-hexyloxyethyl]-2-devinyl pyropheophorbide-a", *J. Photochem Photobiol B*. 20(1):55-61 (1993).

Bellnier et al., "The validation of a new vascular damage assay for photodynamic therapy agents", *Photochem Photobiol.*, 62(5):896-905 (1995).

Bellnier et al., "Protection of murine foot tissue and transplantable tumor against Photofrin-II-mediated photodynamic sensitization with WR-2721", *Journal of Photochemistry and Photobiology B. Biology* 4:219-225 (1989).

Bellnier et al. "An assay for the quantitation of Photofrin in tissues and fluids", *Photochem Photobiol*. 66(2):237-244 (1997).

Bellnier et al., "Distribution and elimination of Photofrin II in mice", *Photochemistry and Photobiology* 50(2):221-228 (1989).

Bellnier et al., "Membrane lysis in Chinese hamster ovary cells treated with hemtoporphyrin derivative plus light", *Photochem Photobiol*. 36(1):43-47 (1982).

Bellnier et al., "A preliminary pharmacokinetic study of intravenous Photofrin in patients", *J Clin Laser. Med Surg.*, 14(5):311-4 (1996).

Bellnier et al., "Haematoporphyrin derivative photosensitization and gamma-radiation damage interaction in Chinese hamster ovary fibroblasts", *Int J Radiat Biol Relat Stud Phys Chem Med.* 50(4):659-664 (1986).

Berstein et al., "Photofrin photodynamic therapy for treatment of AIDS-related cutaneous Kaposi's sarcoma", *AIDS*, 13(13):1697-1704 (1999).

Box et al., "Radical ion saturation in some sulfur compounds x-irradiated at 4.2 degrees" *K. Radiat Res.* 51(1):10-14 (1972).

Boyle et al., "Photobleaching of photofrin II as a means of eliminating skin photosensitivity", *Photochemistry and Photobiology*, 46(6):997-1001 (1987).

Brasseur et al., "Photodynamic activities and skin photosensitivity of the bis(dimethylthexylsiloxy)silicon 2,3-naphthalocyanine in mice", *Photochemistry and Photobiology* 62(6):1058-1065 (1995).

Brennan et al., "Preparation of Bispecific Antibodies by Chemical Recombination of Monoclonal Immunoglobulin G, Fragments", *Science*, 229: 81-83 (1985).

Bugelski et al., "Autoradiographic distribution of hematoporphyrin derivative in normal and tumor tissue of the mouse", *Cancer Res.*, 41(11 Pt 1):4606-4612 (1981).

Chen et al., "Effect of meso-substituents on the osmium tetraoxide reaction and pinacol-pinacolone rearrangement of the corresponding vic-dihydroxyporphyrins", *J Org Chem*. 66(11):3930-3939 (2001).

Chen et al., "Bacteriopurpurinimides: highly stable and potent photosensitizers for photodynamic therapy", *J. Med. Chem*. 45:255-258 (2002).

Derwent Astract Accession No. 9432597, for Japanese Patent Application JP 2003146989 published May 21, 2003, entitled "Pyropheophorbides and their use in photodynamic therapy".

Dimitroff et al., "Anti-angiogenic activity of selected receptor tyrosine kinase inhibitors, PD166285 and PD173074: implications for combination treatment with photodynamic therapy", *Investigational New Drugs*, 17:121-135 (1999).

Dissous et al.,*Schistosoma Mansoni* Surface Antigen Defined by a Rat Monoclonal IgG2a,*J. Immunol*. 129: 2232-2234 (1982).

Doiron et al., "Fluorescence bronshoscopy for detection of lung cancer", *Chest*, 76(1):27-32 (1979).

Dougherty TJ, "Transannular peroxides as radiation sensitizers", *Radiat Res.*, 55(1):101-108 (1973).

Dougherty TJ, "A brief history of clinical photodynamic therapy development at Roswell Park Cancer Institute", *J Clin Laser Med Surg*. 14(5):219-221 (1996).

Dougherty TJ, "Use of hematoporphyrin in photodynamic therapy", *J Photochem Photobiol B*. 8(4):439 (1991).

Dougherty TJ, "Photosensitizers: therapy and detection of malignant tumors", *Photochemistry and Photobiology* 45(6):879-889 (1987).

Dougherty TJ, "Activated dyes as antitumor agents", *J Natl Cancer Inst*. 52(4):1333-1336 (1974).

Dougherty TJ, "Photodynamic therapy", *Photochem Photobiol.*, 58(6):895-900 (1993).

Dougherty TJ, "Photodynamic Therapy: Part II", *Seminars in Surgical Oncology*, 11:333-334 (1995).

Dougherty TJ, "Photodynamic therapy: status and potential", *Oncology (Huntingt)*. 3(7):67-73; Discussion 74, 77-78 (1989).

Dougherty TJ, "Photoradiation therapy for cutaneous and subcutaneous malignancies", *J Invest Dermatol*. 77(1):122-124 (1981).

Dougherty TJ, "Photodynamic therapy (PDT) of malignant tumors", *CRC Critical Reviews in Oncology/Hematology* 2(2):83-116 (1984).

Dougherty TJ, "Photoradiation therapy", *Urology*, 23(3 Suppl):61-64 (1984).

Dougherty TJ, "Photosensitization of malignant tumors", *Seminars in Surgical Oncology* 2:24-37 (1986).

Dougherty TJ, "Variability in hematoporphyrin derivative preparations", *Cancer Res*. 42(3):1188 (1982).

Dougherty TJ, "Photoradiation therapy for bronchogenic cancer", *Chest*, 81(3):265-266 (1982).

Dougherty TJ, "Photodynamic therapy—new approaches", *Seminars in Surgical Oncology* 5:6-16 (1989).
Dougherty TJ, "Hematoporphyrin as a photosensitizer of tumors", *Photochem Photobiol.* 38(3):377-379 (1983).
Dougherty TJ, "Photodynamic therapy", *Adv Exp Med Biol.*, 193:313-328 (1985).
Dougherty TJ, "Photodynamic therapy", *Clinics in Chest Medicine*, 6(2):219-236 (1985).
Dougherty TJ, "An update on photodynamic therapy applications", *J Clin Laser Med Surg.* 20(1):3-7 (2002).
Dougherty TJ, "Studies on the structure of porphyrins contained in Photofrin II" *Photochem Photobiol.*, 46(5):569-573 (1987).
Dougherty et al., "Energetics and efficiency of photoinactivation of murine tumor cells containing hematoporphyrin", *Cancer Research* 36:2330-2333 (1976).
Dougherty et al., "Photoradiation therapy. II. Cure of animal tumors with hematoporphyrin and light", *Journal of the National Cancer Institute*, 55(1)115-121 (1975).
Dougherty et al., "Photoradiation therapy for the treatment of malignant tumors", *Cancer Res.* 38(8):2628-2635 (1978).
Dougherty et al., "Photodynamic Therapy", *Journal of the National Cancer Institute*, 90(12):889-905 (1998).
Dougherty TJ, "Hematoporphyrin derivative for detection and treatment of cancer", *J Surg Oncol.* 15(3):209-210 (1980).
Dougherty et al., "Photoradiation therapy—clinical and drug advances", *Adv Exp Med Biol.* 160:3-13 (1983).
Dougherty et al., "Photoradiation in the treatment of recurrent breast carcinoma", *J Natl Cancer Inst.*, 62 (2):231-237 (1979).
Dougherty et al., "Cutaneous phototoxic occurrences in patients receiving Photofrin", *Lasers Surg Med.* 10(5):485-488 (1990).
Dougherty et al., "Interstitial photoradiation therapy for primary solid tumors in pets cats and dogs", *Cancer Res.* 41(2):401-404 (1981).
Dougherty, "Photodynamic therapy in gastrointestinal cancer", *Lasers in Surgery and Medicine* 12:114 (1992).
Dougherty et al., "Characterization of intra-tumoral porphyrin following injection of hematoporphyrin derivative or its purified component", *Photochemistry and Photobiology*, 46(1):67-70 (1987).
Dougherty et al., "The role of the peripheral benzodiazepine receptor in photodynamic activity of certain pyropheophorbide ether photosensitizers: albumin site II as a surrogate marker for activity", *Photochem Photobiol.*, 76(1):91-97 (2002).
Dougherty TJ, "An overview of the status of photoradiation therapy", *Prog Clin Biol Res.* 170:75-87 (1984).
Dougherty et al., "Photodynamic therapy", *Eur J Cancer.* 28A(10):1734-1742 (1992).
Dougherty et al., "The structure of the active component of hematoporphyrin derivative", *Prog Clin Biol Res.*, 170:301-314 (1984).
Dougherty et al., "Of what value is a highly absorbing photosensitizer in PDT?" *J Photochem Photobiol B.*, 8(2):223-225 (1991).
Douglass et al., "Intra-abdominal applications of hematoporphyrin photoradiation therapy", *Adv Exp Med Biol.*, 160:15-21 (1983).
Farrell et al., "A diffusion theory model of spatially resolved, steady-state diffuse reflectance for the noninvasive determination of tissue optical properties in vivo", *Med. Phys.*, 19(4):879-888 (1992).
Fingar et al., "Drug and light dose dependence of photodynamic therapy: a study of tumor cell clonogenicity and histologic changes,", *Photochem Photobiol.*, 45(5):643-650 (1987).
Flock et al., "Monte Carlo Modeling of Light Propagation in Highly Scattering Tissues—I: Model Predictions and Comparison with Diffusion Theory," *IEEE Transactions on Biomedical Engineering*, 36(12):1162-1168 (1989).
Flock et al., "Monte Carlo Modeling of Light Propagation in Highly Scattering Tissues—II: Comparison with Measurements in Phantoms," *IEEE Transactions on Biomedical Engineering*, 36(12):1169-1173 (1989).
Fukuzumi et al., "Photochemical and electrochemical properties of zinc chlorin-C60 dyad as compared to corresponding free-base chlorin-C60, free-base porphyrin-C60, and zinc porphyrin-C60 dyads", *J Am Chem Soc.*, 123(43):10676-10683 (2001).

Glennie et al., "Preparation and Performance of Bispecific F(ab'γ)$_2$ Antibody Containing Thioether-Linked Fab'γ Fragments", *J. Immunol.*, 139:2367-2375 (1987).
Gomer CJ et al., "Determination of [3H]- and [14C]hematoporphyrin derivative distribution in malignant and normal tissue", *Cancer Res.* 39(1):146-151 (1979).
Graham et al., "Structure-activity relationship of new octaethylporphyrin-based benzochlorins a photosensitzers for photodynamic therapy", *Photochem Photobiol.* 77(5):561-566 (2003).
Gryshuk et al., "A first comparative study of purpurinimide-based fluorinated vs. nonfluorinated photosensitizers for photodynamic therapy", *Photochem Photobiol.*, 76(5):555-559 (2002).
Gryzch et al., "In Vitro and In Vivo Effector Function of Rat IgG2a Monoclonal Anti-*S. Masoni* Antibodies", *J. Immunol.* 129: 2739-2743 (1982).
Henderson et al., "Tumor destruction and kinetics of tumor cell death in two experimental mouse tumors following photodynamic therapy", *Cancer Res.*, 45(2):572-576 (1985).
Henderson et al., "Interaction of photodynamic therapy and hyperthermia: tumor response and cell survival studies after treatment of mice in vivo", *Cancer Res.*, 45(12 Pt 1):6071-6077 (1985).
Henderson et al., "Bacteriochlorophyll-*a* as photosensitizer for photodynamic treatment of transplantable murine tumors", *J. Photochem. Photobiol. B: Biol.* 10:303-313 (1991).
Henderson et al., "An in vivo quantitative structure-activity relationship for a congeneric series of pyropheophorbide derivatives as photosensitizers for photodynamic therapy", *Cancer Res.* 57(18):4000-4007 (1997).
Henderson et al., "How does photodynamic therapy work?" *Photochem Photobiol.* 55(1):145-157 (1992).
Henderson et al., "Aspects of the cellular uptake and retention of hematoporphyrin derivative and their correlation with the biological response to PRT in vitro", *Adv Exp Med Biol.*, 160:129-38 (1983).
Henderson et al. "Studies on the mechanism of tumor destruction by photoradiation therapy", *Prog Clin Biol Res.* 170:601-612 (1984).
Herrera-Ornelas et al., Photodynamic therapy in patients with colorectal cancer *Cancer*, 57(3):677-684 (1986).
Ho et al., "Some components of the tumor-localizing fraction of hematoporphyrin derivative", *Photochemistry and Photobiology*, 52(6):1085-1088 (1990).
Ho et al., "Carbon-14 labeling and biological activity of the tumor-localizing derivate of hematoporphyrin", *Photochem Photobiol.* 48(4):445-449 (1988).
Ho et al., "Activity and physicochemical properties of Photofrin", *Photochem Photobiol.* 54(1):83-87 (1991).
IUPAC-IUB Commission on Biochemical Nomenclature (see, Biochem. 11: 942-944 (1972).
Karpovsky et al., "Production of Target-Specific Effector Cells Using Hetero-Cross-Linked Aggregates Containing Anti-Target Cell and Anti-Fcγ", *J. Exp. Med*. 160:1686 (1984).
Kasper et al., "Isolation and Characterization of A Monoclonal Antibody-Resistant Antigenic Mutant of *Toxoplasma Gondii*", *J. Immunol.* 129: 1694-1699 (1982).
Kessel et al., "Photosensitization with bacteriochlorins", *Photochem Photobiol.*, 58(2):200-203 (1993).
Kessel et al., "Photosensitization by diporphyrins joined via methylene bridges", *Photochemistry and Photobiology* 48(6):741-744 (1988).
Kessel et al., "Photosensitization by synthetic diporphyrins and dichlorins in vivo and in vitro", *Photochemistry and Photobiology* 53(4):475-479 (1991).
Khan et al., "An evaluation of photodynamic therapy in the management of cutaneous metastases of breast cancer", *Eur J Cancer.* 29A(12):1686-1690 (1993).
Kher et al., "Mechano and thermoluminescence of gamma-irradiated CaS04:Dy phosphor.", *Radiat Prot Dosimetry.* 100(1-4):281-284 (2002).
Kozyrev et al., "Thermolysis of vic-dihydroxybacteriochlorins: a new approach for the synthesis of chlorin-chlorin and chlorin-porphyrin dimers", *Org Lett.* 1(8):1193-1196 (1999).
Lele et al., "Photodynamic therapy in gynecologic malignancies", *Gynecol Oncol.* 34(3):350-352 (1989).

Li et al., "A novel synthetic route to fused propenochlorin and benzochlorin photodynamic therapy probes", *Chem Commun (Camb)*. (11):1172-1173 (2002).

Li et al., "Thermolysis of vic-dihydroxybacteriochlorins: effect of the nature of substrates in directing the formation of chlorin-chlorin dimers with fixed and flexible orientations and their preliminary in vitro photosensitizing efficacy", *J Org Chem*. 68(10):3762-3772 (2003).

Li et al., "A simple and efficient approach for the synthesis of fluorinated and nonfluorinated octaethylporphyrin-based benzochlorins with variable lipophilicity, their in vivo tumor uptake, and the preliminary in vitro photosensitizing efficacy", *J Org Chem*. 66(4):1316-1325 (2001).

Liu, Ma et al., "Heteroantibody duplexes target cells for lysis by cytotoxic T lymphocytes", *Proc. Natl. Acad. Sci. USA* 82:8648-8652 (1985).

Lobel et al., "2-[1-hexyloxyethyl]-2-devinyl pyropheophorbide-a (HPPH) in a nude rate glioma model: implications for photodynamic therapy", *Lasers Surg Med*. 29(5):397-405 (2001).

MacDonald et al., "Subcellular localization patterns and their relationship to photodynamic activity of pyropheophorbide-a derivatives", *Photochem Photobiol*. 70(5):789-797 (1999).

Mang et al., "Photobleaching of porphyrins used in photodynamic therapy and implications for therapy", *Photochemistry and Photobiology*, 45(4):501-506 (1987).

Mang et al., "Time and sequence dependent influence of in vitro photodynamic therapy (PDT) survival by hyperthermia", *Photochem Photobiol.*, 42(5):533-540 (1985).

Mang et al., "Fluorescence detection of tumors. Early diagnosis of microscopic lesions in preclinical studies", *Cancer* 71(1):269-276 (1993).

Merrifield et al., "Design and synthesis of antimicrobial peptides", *Ciba Foundation Symposium*, 186:5-20 (1994).

Mettath et al., "DNA interaction and photocleavage properties of porphyrins containing cationic substituents at the peripheral position" *Bioconjugate Chem.*, 10:94-102 (1999).

Mettath et al., "Effect of substituents in directing the formation of benzochlorins isobacteriochlorins in porphyrin and chlorin systems", *Organic Letters* 1(12):1961 (1999).

Milstein et al., "Hybrid hybridomas and the production of bi-specific monoclonal antibodies",*Immunol. Today* 5:299-305 (1984).

Moesta et al., "Protoporphyrin IX occurs naturally in colorectal cancers and their metastases", *Cancer Research*, 61:991-999 (2001).

Morgan et al., "Comparison of photodynamic targets in a carcinoma cell line and its mitochondrial DNA-deficient derivative", *Photochemistry and Photobiology*, 71(6):747-757 (2000).

Morrison and Boyd, *Organic Chemistry*, (5th Ed., 1987), Chapter 13, entitled "Aromaticity," pp. 477-497.

Moskal et al., "Operation and photodynamic therapy for pleural mesothelioma: 6-year follow-up", *Ann Thorac Surg.*, 66:1128-1133 (1998).

Nambisan et al., "Intraoperative photodynamic therapy for retroperitoneal sarcomas", *Cancer*, 61(6):1248-1252 (1988).

Niedre et al., "Direct Near-infrared Luminescence Detection of Singlet Oxygen Generated by Photodynamic Therapy in Cell in Vitro and Tissues In Vivo", *Photochemistry and Photobiology*, 75(4):382-391 (2002).

Nogrady, Medicinal Chemistry A Biochemical Approach, Oxford University Press, New York, pp. 388-392 (1985).

North et al. "Viral Inactivation in Blood and Red Cell Concentrates with Benzoporphyrin Derivative", *Blood Cells* 18:129-40 (1992).

Nseyo et al., "Study of factors mediating effect of photodynamic therapy on bladder in canine bladder model", *Urology*, 32(1):41-45 (1988).

Nseyo et al., "Whole bladder photodynamic therapy for transitional cell carcinoma of bladder", *Urology*, 26(3):274-280 (1985).

Nseyo et al., "Photodynamic therapy in the management of resistant lower urinary tract carcinoma", *Cancer* 60:3113-3119 (1987).

Nseyo et al., "Photodynamic therapy (PDT) in the treatment of patients with resistant superficial bladder cancer: a long-term experience", *Journal of Clinical Laser Medicine Surgery*, 16(1):61-68 (1998).

Nseyo et al., "Dihematoporphyrin ether clearance in primate bladders", *The Journal of Urology*, 136:1363-1366 (1986).

Nseyo et al., "Experimental photodynamic treatment of canine bladder", *J Urol.*, 133(2):311-315 (1985).

Paajanen et al., "Proton Relaxation Enhancement of Albumin, Immunoglobulin G, and Fibrinogen Labeled with Gd-DTPA",*Magn. Reson. Med* 13: 38-43 (1990).

Pandey et al., "Synthesis and photosensitizing activity of a di-porphyrin ether", *Chemical Abstracts*, 109:320 (1988).

Pandey et al., "Synthesis, photophysical properties, in vivo photosensitizing efficacy, and human serum albumin binding properties of some novel bacteriochlorins", *J. Med. Chem*. 40(17):2770-2779 (1997).

Pandey et al., "Chlorin and porphyrin derivatives as potential photosensitizers in photodynamic therapy", *Photochemistry and Photobiology* 53(1):65-72 (1991).

Pandey et al. (1999).

Pandey et al., "Syntheses and photosensitizing activity of porphyrins joined with ester linkages", *Cancer Research* 49:2042-2047 (1989).

Pandey et al., "Evaluation of new benzoporphyrin derivatives with enhanced PDT efficacy", *Photochemistry and Photobiology* 62(4):764-768 (1995).

Pandey et al., "Alkyl ether analogs of chlorophyll-a derivatives: Part I. Synthesis, photophysical properties and photodynamic efficacy", *Photochemistry and Photobiology* 64(1):194-204 (1996).

Pandey et al., "Porphyrin dimers as photosensitizers in photodynamic therapy", *J. Med. Chem*. 33:2032-2038 (1990).

Pandey et al., "Fast atom bombardment mass spectral analyses of Photofrin II and its synthetic analogs", *Biomedical and Environmental Mass Spectrometry* 19:405-414 (1990).

Pandey et al., "Comparative in vivo sensitizing efficacy of porphyrin and chlorin dimers joined with ester, ether, carbon-carbon or amide bonds" *Journal of Molecular Rec* 9:118-122 (1996).

Pierce Chemical Co. catalog, pp. O-90 to O-110 (1995, Pierce Chemical Co., 3747 N. Meridian Rd., Rockford Ill., 61105, U.S.A.).

Polin, R.A. "Monoclonal Antibodies Against Microorganisms", *Eur. J. Clin. Microbiol.*, 3(5): 387-398 (1984).

Potter et al., "The theory of photodynamic therapy dosimetry: consequences of photo-destruction of sensitizer", *Photochemistry and Photobiology* 46(1): 97-101 (1987).

Potter et al., "Photofrin II levels by in vivo fluorescence photometry", *Prog Clin Biol Res*. 170:177-186 (1984).

Potter et al., "Parabolic quantitative structure-activity relationships and photodynamic therapy: application of a three-compartment model with clearance to the in vivo quantitative structure-activity relationships of a congeneric series of pyropheophorbide derivatives used as photosensitizers for photodynamic therapy", *Photochemistry and Photobiology* 70(5):781-788 (1999).

Prakash, G.K.S. and A.K. Yudin, "Perfluoralkylation with Organosilicon Reagents", *Chem Rev.*, 97:757-786 (1997).

Pykett, "NMR Imaging in Medicine", *Scientific American* 246: 78 (1982).

Rakestraw, et al., "Antibody-targeted photolysis: In vitro studies with Sn(IV) chlorin e6 covalently bound to monoclonal antibodies using a modified dextran carrier", *Proc. Nad. Acad. Sci. USA* 87: 4217-4221 (1990).

Ris et al., "Absence of rhodamine 123-photochemotoxicity in human tumor xenografts", *Lasers Surg Med*. 13(1):40-44 (1993).

Roy et al., "Ceramic-Based nanoparticles Entrapping Water-Insoluble Photosensitizing Anticancer Drugs: A Novel Drug-Carrier System for Photodynamic Therapy", *J Am Chem Soc*. 125(26):7860-7865 (2003).

Runfola et al., "Photodynamic therapy for residual neoplasms of the perianal skin", *Dis Colon Rectum*. 43(4):499-502 (2000).

Runge et al., "Paramagnetic Agents for Contrast-Enhanced NMR Imaging: A Review",*Am. J. Radiol*. 141: 1209 (1983).

Rungta et al., "Purpurinimides as photosensitizers: effect of the presence and position of the substituents in the in vivo photodynamic efficacy", *Bioorg Med Chem Lett*. 10(13):1463-1466 (2000).

Schuh et al., "Photodynamic therapy for palliation of locally recurrent breast carcinoma", *Journal of Clinical Oncology* 5(11):1766-1770 (1987).

Senge et al., "Comparative Analysis of the Conformations of Symmetrically and Asymmetrically Deca- and Undecasubstituted Porphyrins Bearing Meso-Alkyl or -Aryl Groups", *Inorg. Chem.*, 36:1149-1163 (1997).

Sery et al., "Photoradiation of rabbit ocular malignant melanoma sensitized with hematoporphyrin derivative", *Curr Eye Res.* 3(4):519-528 (1984).

Sharman et al., "Photodynamic therapeutics: basic principles and clinical applications", *Curr. Trends Drug Discovery Today* 4, 507 (1999).

Siegel et al., "Comparative mass spectrometric analyses of Photofrin oligomers by fast atom bombardment mass spectrometry, UV and IR matrix-assisted laser desorption/ionization mass spectrometry, electrospray ionization mass spectrometry and laser desorption/jet-cooling photoionization mass spectrometry", *J Mass Spectrom.* 34(6):661-669 (1999).

Simpson et al., Isolation and partial characterization of the tegumental outer membrane of adult *Schistosoma mansoni*,*Parasitology* 83: 163-177 (1981).

Singh et al., "Thiocarbamate linkage as internucleoside bond", *Indian J Biochem Biophys.* 33(5):425-427 (1996).

Smith et al., "Passive immunization of mice against *Schistosome mansoni* with an IgM monoclonal antibody",*Parasitology* 84: 83-91 (1982).

Smith, et al., "*Meso* Substitution of Chlorophyll Derivatives: Direct Route for Transformation of Bacteriopheophorbides *d* into Bacteriopheophorbides *c* ", *J. Am. Chem. Soc.* 107: 4946-4954 (1985).

Svaasand et al., "Temperature rise during photoradiation therapy of malignant tumors", *Med Phys.* 10(1):10-17 (1983).

Takita et al., "Intracavitary photodynamic therapy for malignant pleural mesothelioma", *Semin Surg Oncol.* 11:368-371 (1995).

Takita et al., "Operation and intracavitary photodynamic therapy for malignant pleural mesothelioma: a phase II study",*Ann Thorac Surg.* 58(4):995-998 (1994).

Tsuchida et al., "Correlation between site II-specific human serum albumin (HSA) binding affinity and murine in vivo photosensitizing efficacy of some Photofrin components", *Photochemistry and Photobiology* 66(2):224-228 (1997).

Umemura et al., *Ultrasonics Sonochemistry* 3: S187-S191 (1996).

Valenzo et al. eds. (1991).

Van Lier, J.E. "Photosensitization: Reaction Pathways", *Photobiological Techniques* 216: 85-98 (1991).

Vincent et al., "Photoradiation therapy in advanced carcinoma of the trachea and bronchus", *Chest*, 85(1):29-33 (1984).

Vincent et al., "Hematoporphyrin derivative in the diagnosis and treatment of lung cancer", *Adv Exp Med Biol.* 160:41-46 (1983).

Waldow et al., "Interaction of hyperthermia and photoradiation therapy" *Radiat Res.* 97(2):380-385 (1984).

Waldow et al., "Potentiation of photodynamic therapy by heat: effect of sequence and time interval between treatments in vivo", 6*Lasers Surg Med.* 5(2):83-94 (1985).

Waldow et al., "Enhanced tumor control following sequential treatments of photodynamic therapy(PDT) and localized microwave hyperthermia in vivo", *Lasers Surg Med.* 4(1):79-85 (1984).

Waldow et al., "Hyperthermic potentiation of photodynamic therapy employing Photofrin I and II: comparison of results using three animal tumor models", *Lasers Surg Med.* 7(1):12-22 (1987).

Weishaupt et al., "Identification of singlet oxygen as the cytotoxic agent in photoinactivation of a murine tumor", *Cancer Res.*, 36(7 PT 1):2326-2329 (1976).

Wilson et al., "The physics of photodynamic therapy," *Phys. Med. Biol.*, 31(4):327-360 (1986).

Wilson et al., "Photodynamic therapy for the treatment of basal cell carcinoma", *Arch Dermatol.* 128:1597-1601 (1992).

Wood et al., "A beam-splitting device for use with fiber-coupled laser light sources for photodynamic therapy", *Photochem Photobiol.*, 76(6):683-685 (2002).

Yoshida et al., "Hybridoma Produces Protective Antibodies Directed Against the Sporozoite Stage of Malaria Parasite", *Science*, 207:71-73 (1980).

Yumita et al., Sonodynamically induced antitumor effect of gallium-porphyrin complex by focused ultrsound on experimental kidney tumor *Cancer Letters* 1,2: 79-86 (1997).

Yumita et al., "The Comination Treatment of Ultrasound and Antitumor Drugs on Yoshida Sarcoma", *Japan J. Hyperthermic Oncology* 3(2):175-182 (1987).

Zheng et al., "A Simple and Short Synthesis of Divinyl Chlorophyll Derivatives", *J Org Chem.* 64:3751-3754 (1999).

Zheng et al., "Synthesis of beta-galactose-conjugated chlorins derived by enyne metathesis as galectin-specific photosensitizers for photodynamic therapy", *J Org Chem.* 66(26):8709-8716 (2001).

Zheng et al., "Synthesis, photophysical properties, tumor uptake, and preliminary in vivo photosensitizing efficacy of a homologous series of 3-(1'-alkyloxy)ethyl-3-devinylpurpurin-18-$N$-alkylimides with variable lipophilicity", *J Med Chem.* 44:1540-1559 (2001).

Zheng et al., "Photosensitizers related to purpurin-18-$N$-alkylimides: a comparative in vivo tumoricidal ability of ester versus amide functionalities", *Bioorganic & Medicinal Chemistry Letters*, 10:123-127 (2000).

Zheng et al., "Wittig reactions on photoprotoporphyrin IX: new synthetic models for the special pair of the photosynthetic reaction center", *J Org Chem.* 65(2):543-557 (2000).

Zodda et al., Monoclonal Antibody-Mediated Protection against *Schistosoma mansoni* Infection in Mice, *J. Immunol.* 129: 2326-2328 (1982).

Anderson et al. "Photodynamic therapy for sarcoma pulmonary metastases: a preclinical toxicity study," *Anticancer Res.* 23:3713-3718 (2003).

Certified English Translation of: Fischer, H. et al., "[On the Bromination of the Esters of Mesoisochlorin e4 and Mesochlorin e6]," *Berischte der Deutschen Chemischen* 75:1778-1795 (1942).

Chen et al., "New directions in photodynamic therapy," *ICCP-2. 2nd International Conference on Porphyrins and Phthalocyanines*, Jun. 30, 2002-Jul. 5; Kyoto, Japan: 78 [abstract S-26].

Chen et al., "New technology for deep light distribution in tissue for phototherapy," *Cancer J* 8(2):154-163. (2002).

Chen et al., "Next-generation light delivery system for multitreatment extended-duration photodynamic therapy (MED-PDT)," *Proc SPIE* 2972:161-166 (1997).

Database Crossfire Beilstein, Database Acession No. 4286587 (Reaction ID), for Levinson, E.G. et al., Russ. J. Bioorg. Chem (Engl. Transl.) 21(3):199-203 (1995) in Russian in the :Bioorg. Khim. 21(3)230-234 (1995).

Derwent English Abstract, Accession No. 1996-475153, citing Russian Patent RU 2054944 C, published Feb. 27, 1996, "Production of purpurin-18 for treatment of tumours—comprises extracting vegetable waste with ethanol, oxidative splitting, degreasing and purifying".

Fischer, H. et al., "[On the Bromination of the Esters of Mesoisochlorin $e_4$ and Mesochlorin $e_6$]," *Berischte der Deutschen Chemischen* 75:1778-1795 (1942).

Haslam et al., "Recent Developments in Methods for the Esterification and Protection of the Carboxyl Group," *Tetrahedron* 36: 2409-2433 (1980).

Jones et al. "Photodynamic therapy for patients with advanced non-small-cell carcinoma of the lung," *Clin Lung Cancer.* 3(1):37-41 (2001).

Li et al., "Application of Ruppert's reagent in preparing novel perfluorinated porphyrins, chlorins and bacteriochlorins", *J. Chem. Soc. Perkin Trans* 1, 1785-1787 (1999).

Li et al., "Synthesis, comparative photosensitizing efficacy, human serum albumin (site II) binding ability, and intracellular localization characteristics of novel benzobacteriochlorins derived from vic-dihydroxybacteriochlorins," *J Med Chem.* 46(25):5349-5359 (2003).

Lustig et al., "A multicenter Phase I safety study of intratumoral photoactivation of talaporfin sodium in patients with refractory solid tumors," *Cancer* 98(8):1767-71 (2003).

Patent Abstract of Japan citing Japanese Patent Application JP 09124652, published May 13, 1997, "Porphyrin Derivative and Use Thereof".

Schmidt-Erfurth et al., "Photodynamic therapy of subfoveal choroidal neovascularization: clinical and angiographic examples," *Graefe's Arch Clin Exp Opthalmol.* 236:365-374 (1998).

Schmidt-Erfurth et al., "Vascular Targeting in Photodyamic Occlusion of Subretinal Vessels," *Opthalmology* 101:1953-1961 (1994).

Smith et al., "Bacteriochlorophylls c from *Chloropseudomonas ethylicum*. Composition and NMR Studies of the Pheophorbides and Derivatives", Am. Chem. Soc., 102(7):2437-2448 (1980).

Zheng et al., "Chlorin-based symmetrical and unsymmetrical dimers with amide linkages: effect of the substituents on photodynamic and photophysical properties,"*J. Chem. Soc. Perkins 1*, pp. 3113-3121 (2002).

Zheng et al., "PDT using a novel LED light source and LSII in a rat liver model," *30th Annual Meeting of the American Society for Photobiology*; Jul. 13-17, 2002; Quebec City, Canada. American Society for Photobiology:33 [abstract 95].

* cited by examiner

WATER SOLUBLE TETRAPYROLLIC PHOTOSENSITIZERS FOR PHOTODYNAMIC THERAPY

CROSS REFERENCE TO RELATED APPLICATIONS

This is a continuation-in-part of U.S. patent application Ser. No. 10/607,922 to Pandey et al. filed Jun. 27, 2003 now U.S. Pat. No. 7,166,719 entitled FLUORINATED PHOTOSENSITIZERS RELATED TO CHLORINS AND BACTERIOCHLORINS FOR PHOTODYNAMIC THERAPY which in turn claims priority from Provisional Application Ser. No. 60/392,473 to Pandey et al. filed Jun. 27, 2002 entitled FLUORINATED PHOTOSENSITIZERS RELATED TO CHLORINS AND BACTERIOCHLORINS FOR PHOTODYNAMIC THERAPY.

The above applications are incorporated herein by reference in their entirety.

STATEMENT REGARDING FEDERALLY SPONSORED RESEARCH

This invention was made with funding from the National Institute of Health Grant Number NIH CA55791. The United States Government may have certain rights in this invention.

BACKGROUND OF THE INVENTION

For a number of years, attempts have been underway in various laboratories to replace Photofrin® with new porphyrin-based photosensitizers (PS). To date, most PS are amphiphilic in nature in that they contain both hydrophilic and hydrophobic substituents. Due to their #-conjugated systems, a phenomenon known as aggregation has become a concern such that it can: "decrease fluorescence quantum yields, shorten a photosensitizer's triplet excited state lifetime or reduce its photosensitizing efficiency". Most of these compounds, therefore, are visibly aggregated in solution, so the challenge remains to be the synthesis of effective water-soluble photosensitizers that accumulate in the tumor, yet clear at a suitable time as to limit toxicity. Several researchers have either incorporated sugar residues on the periphery or ionic groups such as pyridinium, sulfonato or carboxylate groups as a means to enhance photosensitizers' aqueous solubility. The 5, 10, 15, 20-tetrakis(4-sulfonatophenyl)-porphyrin ($TPPS_4$) is a known tetrasodium salt that although soluble in water still absorbs weakly at ~630 nm. Core modifications have been made to $TPPS_4$ in which chalcogen atoms such as sulfur, selenium and tellurium have aided in the water solubility of the PS, as well as, increasing the wavelength maximum to ~695 nm. Unfortunately, these compounds were found to be toxic Therefore, the aim of the present invention was to synthesize effective and non-toxic water-soluble long wavelength absorbing photosensitizers with high singlet oxygen ability, singlet oxygen being a key cytotoxic agent for PDT. Tetrapyrollic compounds, especially porphyrin related compounds, have played a key role in developing a variety of photosensitizers. Inventors herein have recently shown that porphyrin-based compounds can also be used (i) as PET and SPECT imaging agents and (ii) as vehicles to deliver the required contrast agents (MRI, Fluorescence etc.) to image tumors. These approaches have been extremely useful in developing multimodality agents. However, one major drawback with most of these compounds is their limited solubility in water. Therefore, most of the formulations require a biocompatible surfactant, e.g. such as those commonly sold under the trademarks TWEEN-80 or CREMOPHORE. At low concentrations, such formulations are approved by FDA for clinical use, but to avoid a number of disadvantages with such formulations, it would be 'ideal' to design water soluble compounds for tumor imaging and therapy.

An approach for increasing the water solubility is to introduce hydrophilic substituents (e.g., —COOH, PEG, amino acids, charged species etc.) in the desired molecules. Unfortunately such incorporation can limit biological efficacy.

The following references are incorporated by reference as background art.

1. R. K. Pandey, G. Zheng The Porphyrin Handbook (Eds: Kadish, Rodgers and Smith), vol. 6, Academic Press, Boston, 2000.
2. Suresh K. Pandey, Amy L. Gryshuk, Munawwar Sajjad, Xiang Zheng, Yihui Chen, Mohei M. Abouzeid, Janet Morgan, Ivan Charamisinau, Hani A. Nabi, Allan Oseroff and Ravindra K. Pandey, Multiomodality Agents for Tumor Imaging (PET, Fluorescence) and Photodynamic Therapy: A Possible See and Treat Approach. *J. Med. Chem.* 2005, 48, 6286-6295.
3. Ravindra K. Pandey et al., Chlorophyll-a Analogs Conjugated with Aminophenyl-DTPA as Potential Bifunctional Agents for Magnetic Resonance Imaging and Photodynamic Therapy. *Bioconjugate Chem.* 2005, 16, 32-42.
4. Ravindra K. Pandey, A. B. Sumlin, W. R. Potter, D. A. Bellnier, B. W. Henderson, S. Constantine, M. Aoudia, M. R. Rodgers, K. M. Smith and T. J. Dougherty, Structure and Photodynamic Efficacy Among Alkyl Ether Analogues of Chlorophyll-a Derivatives. *Photochem. Photobiol.* 1996, 63, 194-205.
5. Gang Zheng, Susan Camacho, William Potter, David A. Bellnier, B. W. Henderson, Thomas J. Dougherty and Ravindra K. Pandey, Synthesis, tumor uptake and in vivo photosensitizing efficacy of a homologous series of the 3-(1'-alkoxy)ethyl-purpurin-18-N-alkylimides, *J. Med Chem*, 2001, 44, 1540-1559.
6. Yihui Chen, Andrew Graham, William Potter, Janet Morgan, Lurine Vaughan, David A. Bellnier, Barbara W. Henderson, Allan Oseroff, Thomas J. Dougherty and Ravindra K. Pandey, *J. Med Chem*. (*Rapid Communication*), 2002, 45, 255-258.

BRIEF DESCRIPTION OF THE DRAWINGS

FIG. 5 shows In vivo quantitation of PS 16 fluorescence normalized to controls (ex: 417 nm; em: ~710 nm).

BRIEF DESCRIPTION OF THE INVENTION

Figure 1A:
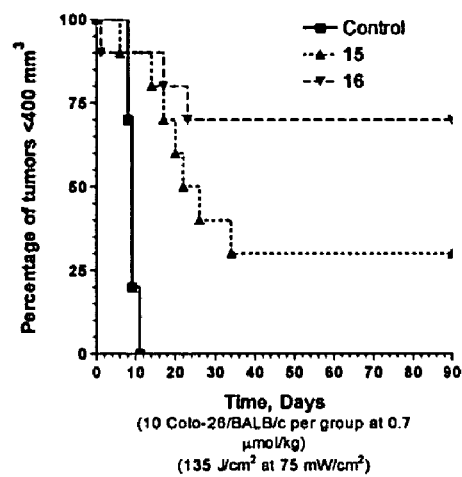
FIG. 1A shows a graph of In vivo photosensitizing efficacy of PS 15 and the corresponding water-soluble analog PS 16 (24 h p.i.) BALB-C mice were implanted with Colo-26 tumors. The tumors were exposed with laser light (135 $J/cm^2$, 75 $mW/cm^2$ for 30 min) 24 h post injection.
Figure 1B:
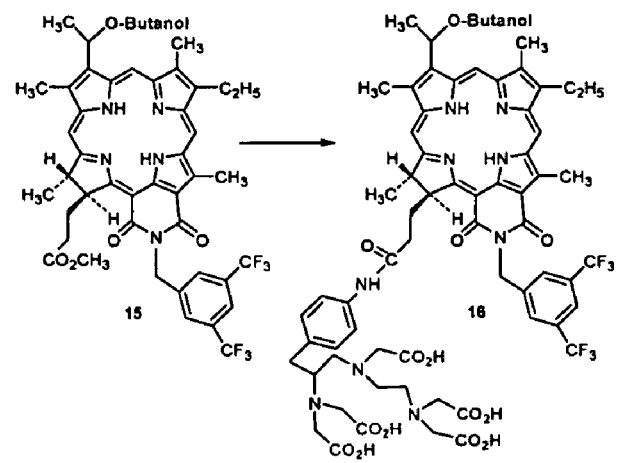
FIG. 1B shows a schematic preparation of compound 16 from compound 15.
Figure 2:
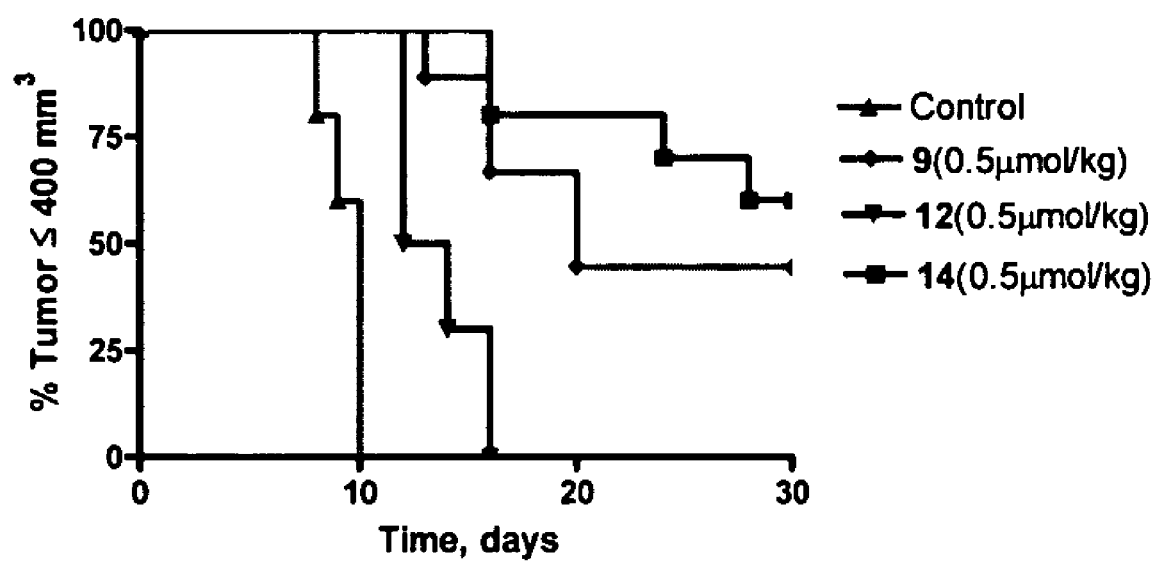
FIG. 2 shows a graph of In vivo photosensitizing efficacy of compounds 9, 12 and 14. BALB-C mice were implanted with Colo-26 tumors. The tumors were exposed with laser light (135 $J/cm^2$, 75 $mW/cm^2$ for 30 min) 24 h post injection.

In accordance with the present invention, a series of water soluble purpurinimides were prepared and some of these compounds were found to be quite effective both for PDT efficacy and tumor imaging (fluorescence).

The photosensitizers are tetrapyrollic photosensitizers having at least one pendant —$CH_2CH_2CON(CH_2CON(CH_2COOH)_2)_2$ or —$N(CH_2COOH)_2$ group or esters thereof. The substituted tetrapyrollic compound is usually a chlorin, bacteriochlorin, porphyrin, pyropheophorbide, purpurinimide, or bacteriopurpurinimide.

DETAILED DESCRIPTION OF THE INVENTION

In a preferred embodiment the compound of the invention has the formula:

[Chemical structure of tetrapyrrolic compound with substituents $R_1$, $R_{1a}$, $R_2$, $R_{2a}$, $R_3$, $R_{3a}$, $R_4$, $R_{4a}$, $R_5$, $R_6$, $R_{6a}$, $R_7$, $R_8$, $R_{8a}$, $R_9$, $R_{10}$ on rings a, b, c, d]

or a phamaceutically acceptable derivative thereof.

$R_1$ and $R_2$ are each independently substituted or unsubstituted alkyl, substituted or unsubstituted alkenyl, —$C(O)R_a$ or —$COOR_a$ or —$CH(CH_3)(OR)$ or —$CH(CH_3)(O(CH_2)_nXR)$ where $R_a$ is hydrogen, substituted or unsubstituted alkyl, substituted or unsubstituted alkenyl, substituted or unsubstituted alkynyl, or substituted or unsubstituted cycloalkyl where $R_2$ may be $CH=CH_2$, $CH(OR_{20})CH_3$, $C(O)Me$, $C(=NR_{21})CH_3$ or $CH(NHR_{21})CH_3$.

X is an aryl or heteroaryl group.

n is an integer of 0 to 6.

R and R' are independently H or lower alkyl of 1 through 8 carbon atoms.

$R_{20}$ is methyl, butyl, heptyl, docecyl or 3,5-bis(trifluoromethyl)-benzyl.

$R_{21}$ is 3,5,-bis(trifluoromethyl)benzyl.

$R_{1a}$ and $R_{2a}$ are each independently hydrogen or substituted or unsubstituted alkyl, or together form a covalent bond.

$R_3$ and $R_4$ are each independently hydrogen or substituted or unsubstituted alkyl.

$R_{3a}$ and $R_{4a}$ are each independently hydrogen or substituted or unsubstituted alkyl, or together form a covalent bond.

$R_5$ is hydrogen or substituted or unsubstituted alkyl.

$R_6$ and $R_{6a}$ are each independently hydrogen or substituted or unsubstituted alkyl, or together form =O.

$R_7$ is a covalent bond, alkylene, azaalkyl, or azaaraalkyl or =$NR_{20}$ where $R_{20}$ is hydrogen or lower alkyl of 1 through 8 carbon atoms or —$CH_2$-3,5-bis(tri-fluoromethyl)benzyl or —$CH_2X$—$R_1$ or —$YR^1$ where Y is an aryl or heteroaryl group.

$R_8$ and $R_{8a}$ are each independently hydrogen or substituted or unsubstituted alkyl or together form =O.

$R_9$ is —$CH_2CH_2CON(CH_2CON(CH_2COOA)_2)_2$ or —$N(CH_2COOH)_2$; where A is —OH or -lower alkyl.

$R_{10}$ is hydrogen, or substituted or unsubstituted alkyl.

Each of $R_1$-$R_{10}$, when substituted, is substituted with one or more substituents each independently selected from Q, where Q is alkyl, haloalkyl, halo, pseudohalo, or —$COOR_b$ where $R_b$ is hydrogen, alkyl, alkenyl, alkynyl, cycloalkyl, aryl, heteroaryl, araalkyl, or $OR_c$ where $R_c$ is hydrogen, alkyl, alkenyl, alkynyl, cycloalkyl, or aryl or —$CONR_dR_e$ where $R_d$ and $R_e$ are each independently hydrogen, alkyl, alkenyl, alkynyl, cycloalkyl, or aryl, or —$NR_fR_g$ where $R_f$ and $R_g$ are each independently hydrogen, alkyl, alkenyl, alkynyl, cycloalkyl, or aryl, or =$NR_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, pseudohalo, or —$COOR_b$ where $R_b$ is hydrogen, alkyl, alkenyl, alkynyl, cycloalkyl, aryl, heteroaryl, araalkyl, or $OR_c$ where $R_c$ is hydrogen, alkyl, alkenyl, alkynyl, cycloalkyl, or aryl or $CONR_dR_e$ where $R_d$ and $R_e$ are each independently hydrogen, alkyl, alkenyl, alkynyl, cycloalkyl, or aryl, or $NR_fR_g$ where $R_f$ and $R_g$ are each independently hydrogen, alkyl, alkenyl, alkynyl, cycloalkyl, or aryl, or =$NR_h$ where $R_h$ is hydrogen, alkyl, alkenyl, alkynyl, cycloalkyl, or aryl, or is an amino acid residue.

Synthetic details for the preparation of examples of water soluble photosensitizers of the invention are depicted in Schemes 1-4 as follow:

Scheme 1

[Reaction scheme showing compound 1 (HN(CH_2CO_2H)_2) converted via step a) to compound 2 (Cbz-N(CH_2CO_2H)_2), then via step b) to compound 3 (a Cbz-protected intermediate with tert-butyl ester groups), then via step c)]

-continued
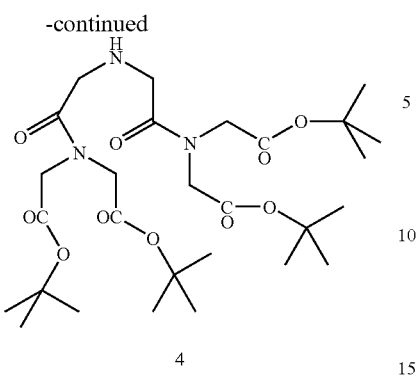
4
Reagents: a) Cbz-Cl, KHCO₃, H₂O, 0° C., RT, 6 hr
b) Di-tert-butyl iminodiacetate, EDCl, DMAP, Dry DCM, RT, 16 hr
c) Pd/C 10%, MeOH, H₂, 2 hr, RT
Scheme 2
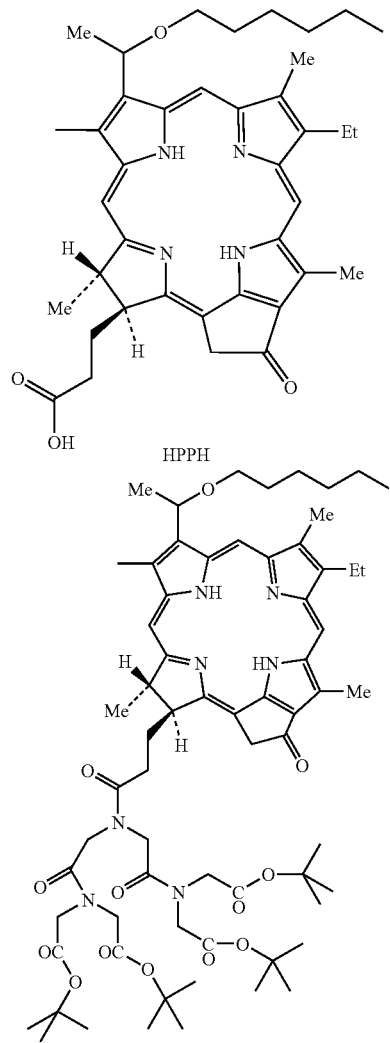
HPPH
5
-continued
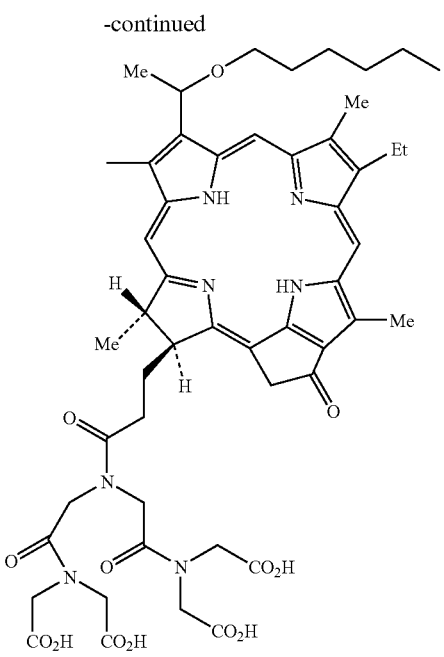
6
Reagents: a) 3, EDCl, DMAP, Dry DCM, RT, 16 hr
b) 70% TFA/DCM, 3 hr, RT
Scheme 3
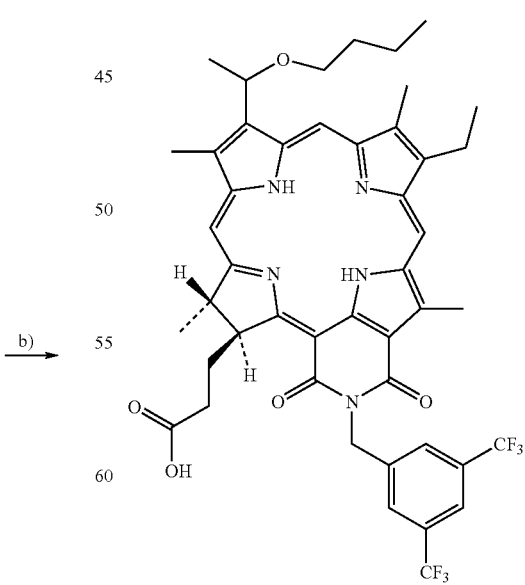
7

-continued
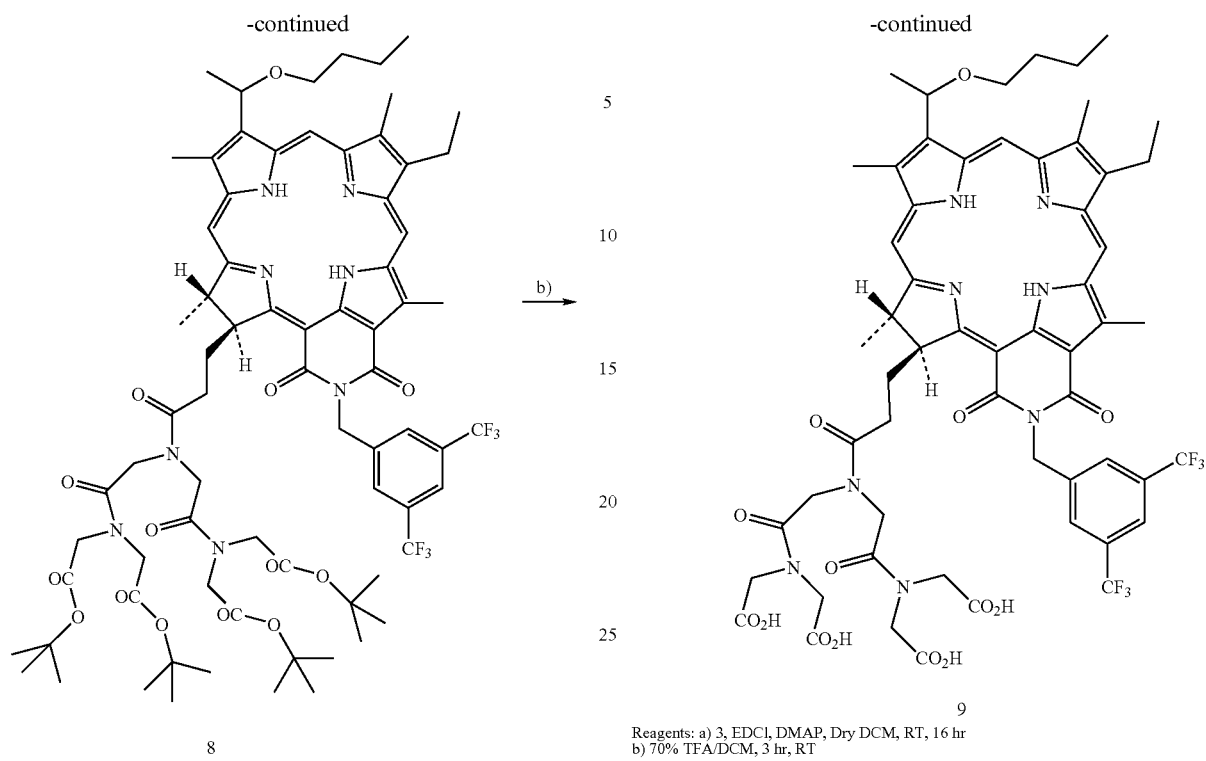
8
Reagents: a) 3, EDCl, DMAP, Dry DCM, RT, 16 hr
b) 70% TFA/DCM, 3 hr, RT
Scheme 4
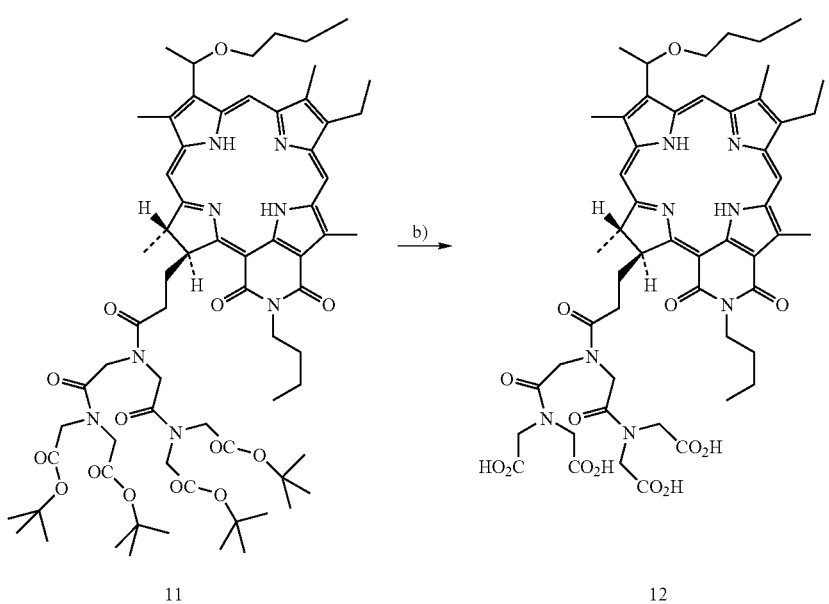

-continued

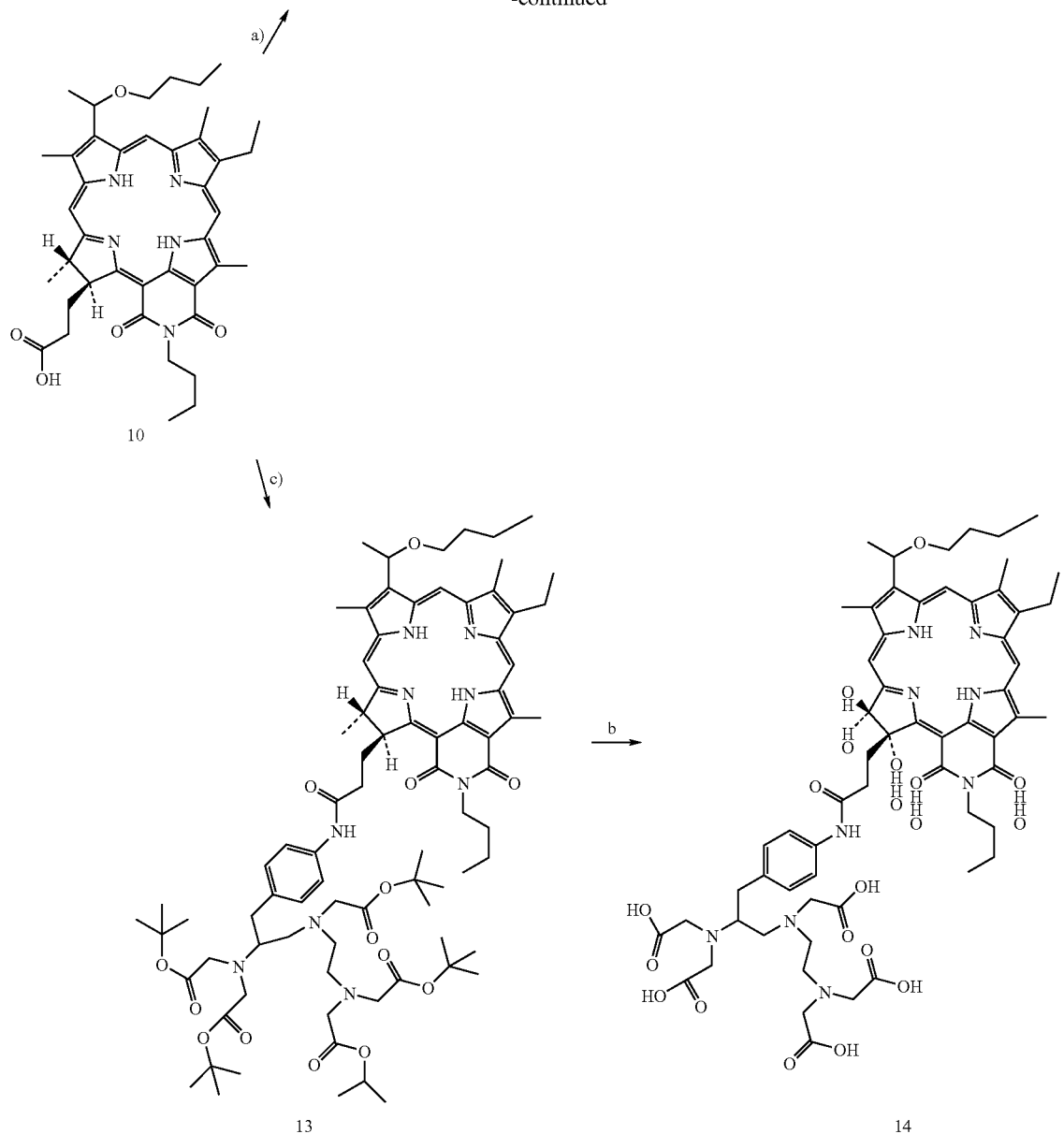

Reagents: a) 3, EDCl/DMAP, Dry DCM, RT, 16 hr
b) 70% TFA/DCM, 3 hr, RT
c) aminobenzyl DTPA(tBu), EDCl, DMAP, Dry DCM, RT, 16 hr All the intermediates and the final products were characterized by NMR and mass spectrometry analyses. The purity was ascertained by analytical TLC. The starting photosensitizers (e.g. HPPH, fluorinated purpurinimide 7 and the N-butyl-purpurinimide 10 were synthesized by following published methodologies that were developed in our laboratory) The Synthetic details are as follows:

Compound No. 2

Iminodiacetic acid (5.0 gm, 0.03756 mole) was taken in a 500 ml RBF, water (150 ml) and THF (50 ml) were added to it. Resultant mixture was cooled to 0° C. using an ice bath. $K_2CO_3$ (25.9 gm, 0.187 mole) was added to it in portions keeping temperature of reaction mixture below 10° C. After 10 min of stirring at the same temperature Cbz-Cl (7.9 ml, 0.056 mole) was added to it drop wise. Resultant mixture was stirred for 6 hr at room temperature, concentrated partially to remove THF. Reaction mixture was washed with ether to remove excess of Cbz-Cl, aq layer was separated, acidified with dil HCl and extracted with EtOAc (100 ml×3). Organic layers were separated, combined and washed with $H_2O$ (100 ml), dried over sodium sulfate and concentrated to give 2 as viscous oil in quantitative yield.

Yield: 9.6 gm (95.7%).

$^1$HNMR (400 MHz, $CDCl_3$): δ 7.36-7.30 (m, 5H, Ph), 5.16 (s, 2H, PhCH$_2$O), 4.15 (s, 2H, CH2), 4.12 (s, 2H, CH$_2$).

EIMS: 267(m$^+$).

Compound No. 3

Di-acid 2 (0.5 gm, 1.88 mmol), Di-tert-butyl iminodiacetate (0.92 gm, 3.77 mmol), EDCI (1.0 gm, 5.6 mmol) and DMAP (0.36 gm, 5.6 mmol) were dissolved in dry DCM (30 ml). Resultant mixture was stirred at room temperature for 16 hr under $N_2$ atm, diluted with DCM (100 ml) and washed with brine (50 ml). Organic layer was separated, dried over sodium sulfate and concentrated. Crude was purified on silica gel column using EtOAc/hexane (20-40%) as eluent to give product 3. Yield: 1.0 gm (75%).

$^1$HNMR (400 MHz, $CDCl_3$): δ 7.34-7.28 (m, 5H, Ph), 5.12 (s, 2H, Ph$\underline{CH_2}$O), 4.28 (d, 1H, J=6.4 Hz), 4.24 (d, 1H, J=6.8 Hz), 4.18-4.14 (m, 1H), 4.05 (m, 4H), 3.91 (m, 1H), 3.74 (d, 1H, J=8.0 Hz), 3.67 (d, 1H, J=10.8 Hz), 1.47 (s, 9H, $CO_2Bu^t$), 1.45 (s, 9H, $CO_2Bu^t$), 1.44 (s, 9H, $CO_2Bu^t$), 1.40 (s, 9H, $CO_2Bu^t$). EIMS: 744(m+$Na^+$).

Compound No. 4

Compound 3 (0.9 gm, 1.24 mmol), Pd/C (10%, 1.0 gm), MeOH (60 ml) were stirred together under $H_2$ atm for 2 hr. Reaction mixture was filtered over celite, filtrate was concentrated and chromatographed over silica get using MeOH/DCM (1-3%) as eluent. Yield: 0.6 gm (82.5%).

$^1$HNMR (400 MHz, $CDCl_3$): δ 4.06 (s, 4H, $CH_2$), 4.01 (s, 4H, $CH_2$), 3.46 (s, 4H, $CH_2$), 1.46 (s, 36H, $CO_2Bu^t$). EIMS: 587($m^+$).

Compound No. 5

HPPH (100.0 mg, 0.157 mmol), amine 4 (184.5 mg, 0.314 mmol), EDCI (90.4 mg, 0.471 mmol) and DMAP (57.5 mg, 0.471 mmol) were dissolved in dry DCM (30 ml). Resultant mixture was stirred at room temperature for 16 hr under $N_2$ atm, diluted with DCM (100 ml) and washed with brine (50 ml). Organic layer was separated, dried over sodium sulfate and concentrated. Crude was purified on silica gel column using MeOH/DCM (1-3%) as eluent to give product 5. Yield: 120.0 mg (63.35%). UV-vis (λmax $cm^{-1}$, dichloromethane): 409, 505, 535, 606 & 661.

$^1$HNMR (400 MHz, $CDCl_3$): δ 9.74 (s, 1H, meso-H), 9.51 (s, 1H, meso-H), 8.52 (s, 1H, meso-H), 5.91 (m, 1H, $CH_3\underline{CH}$Ohexyl), 5.35 (d, 1H, $15^1$-$\underline{CH}$, J=20.0 Hz), 5.13 (d, 1H, $15^1$-$\underline{CH}$, J=20.0 Hz), 4.52-4.49 (m, 2H, H-17 & H-18), 4.29-4.27 (m, 4H), 4.11 (m, 2H), 4.09-4.04 (m, 4H), 3.88-3.85 (m, 2H, $CH_2$), 3.74-3.72 (m, 2H, O$\underline{CH_2}$hexyl), 3.67 (s, 3H, ring-$CH_3$), 3.66-3.59 (m, 2H, $8^1$-$\underline{CH_2}$), 3.36 (s, 3H, ring-$CH_3$), 3.26 (s, 3H, ring-$CH_3$), 2.78-2.66 (m, 2H, $17^2$-$CH_2$), 2.53-2.49 (m, 1H, $17^1$-CH), 2.15 (m, 1H, 17'-CH), 2.11 (d, 3H, $\underline{CH_3}$CHOhexyl, J=6.8 Hz), 1.79 (d, 3H, 18-$CH_3$, J=7.6 Hz), 1.74 (t, 3H, 8-$CH_2\underline{CH_3}$, J=7.6 Hz) 1.63 (m, 4H, $CH_2$-hexyl), 1.47-1.43 (four singlets each for $CO_2Bu^t$, 36H), 1.20 (m, 4H, $CH_2$-hexyl), 0.77 (t, 3H, $CH_3$-hexyl, J=6.4 Hz), 0.37 (brs, 1H, NH), –1.82 (brs, 1H, NH). EIMS: 1206 ($m^+$).

Compound No. 6

Compound 5 (70.0 mg) was stirred in 5 ml of 70% TFA/DCM for 3 hr at room temperature. The reaction mixture was concentrated and dried under high vacuum to give 6 in quantitative yield.

Yield: 50.0 mg (87.7%). UV-vis (λmax $cm^{-1}$, THF): 408, 505, 538, 605 & 660. EIMS: 983 ($m^{30}$+1).

Compound No. 8

Acid 7 (100.0 mg, 0.115 mmol), amine 4 (136.0 mg, 0.231 mmol), EDCI (44.4 mg, 0.231 mmol) and DMAP (28.27 mg, 0.231 mmol) were dissolved in dry DCM (30 ml). Resultant mixture was stirred at room temperature for 16 hr under $N_2$ atm, diluted with DCM (100 ml) and washed with brine (50 ml). Organic layer was separated, dried over sodium sulfate and concentrated. Crude was purified on silica gel column using MeOH/DCM (1-3%) as eluent to give product 8. Yield: 80.0 mg (48%). UV-vis (λmax $cm^{-1}$, dichloromethane): 365, 414, 548 & 701. $^1$HNMR (400 MHz, $CDCl_3$): δ 9.74 (s, 1H, meso-H), 9.60 (s, 1H, meso-H), 8.51 (s, 1H, meso-H), 8.20 (s, 2H, bis-$CF_3C_6H_3$), 7.79 (s, 1H, bis-$CF_3C_6H_3$), 5.79 (s, 2H, benzylic $CH_2$), 5.75 (m, 1H, $CH_3\underline{CH}$Obutyl), 5.19-5.16 (m, 1H, H-17), 4.60-4.49 (m, 2H, $CH_2$), 4.40-4.31 (m, 2H, $CH_2$), 4.18-3.96 (m, 8H, 4$CH_2$), 3.62 (s, 3H, ring-$CH_3$), 3.61-3.60 (m, 4H, 2$CH_2$), 3.26 (s, 3H, ring-$CH_3$), 3.16 (s, 3H, ring-$CH_3$), 2.94-2.87 (m, 1H, $17^2$-CH), 2.76-2.69 (m, 1H, $17^2$-CH), 2.40-2.34 (m, 1H, $17^1$-CH), 2.05 (d, 3H, $\underline{CH_3}$CHObutyl, J=10.2 Hz), 1.77-1.64 (m, 11H, $17^1$-CH, 18-$CH_3$, 2$CH_2$butyl, 8-$CH_2\underline{CH_3}$), 1.48 (s, 9H, $CO_2Bu^t$), 1.46 (s, 9H, $CO_2Bu^t$), 1.39 (s, 9H, $CO_2Bu^t$), 1.38 (s, 9H, $CO_2Bu^t$), 0.89-0.85 (spitted t, 3H, $CH_3$-butyl), 0.21 (brs, 1H, NH), 0.07 (brs, 1H, NH). EIMS: 1403 ($m^+$).

Compound No. 9

Compound 8 (60.0 mg) was stirred in 5 ml of 70% TFA/DCM for 3 hr at room temperature. Reaction mixture was concentrated and dried under high vacuum to give 9 in quantitative yield.

Yield: 40.0 mg (77.36%). UV-vis (λmax $cm^{-1}$, THF): 363, 414, 546 & 699. EIMS: 211 ($m^+$+1).

Compound No. 11

Acid 10 (50.0 mg, 0.072 mmol), amine 4 (84.7 mg, 0.144 mmol), EDCI (34.5 mg, 0.18 mmol) and DMAP (22.0 mg, 0.18 mmol) were dissolved in dry DCM (30 ml). Resultant mixture was stirred at room temperature for 16 hr under $N_2$ atm, diluted with DCM (100 ml) and washed with brine (50 ml). Organic layer was separated, dried over sodium sulfate and concentrated. Crude was purified on silica gel column using MeOH/DCM (1-2%) as eluent to give product 11.

Yield: 65.0 mg (71.42%). UV-vis (λmax $cm^{-1}$, dichloromethane): 363, 415, 508, 547 & 701. $^1$HNMR (400 MHz, $CDCl_3$): δ 9.72 (s, 1H, meso-H), 9.63 (s, 1H, meso-H), 8.52 (s, 1H, meso-H), 5.79 (m, 1H, $CH_3\underline{CH}$Obutyl), 5.22 (m, 1H, H-17), 4.66 (m, 2H, $CH_2$), 4.45 (t, 2H, O$CH_2$butyl, J=7.6 Hz), 4.33 (m, 1H, H-18), 4.18-4.00 (m, 4H, 2$CH_2$), 3.97-3.95 (m, 4H, 2$CH_2$), 3.84 (s, 3H, ring-$CH_3$), 3.68-3.61 (m, 4H, 8-$\underline{CH_2}CH_3$, $CH_2$), 3.30 (s, 3H, ring-$CH_3$), 3.18 (s, 3H, ring-$CH_3$), 3.00-2.90 (m, 1H, $17^2$-CH), 2.74-2.69 (m, 1H, $17^2$-CH), 2.45-2.39 (m, 1H, $17^1$-CH), 2.06 (d, 3H, $\underline{CH_3}$CHObutyl, J=6.8 Hz), 2.01-1.96 (m, 2H, N$CH_2$-butyl), 1.70 (m, 1H, $17^1$-CH), 1.68-1.61 (m, 10H, 18-$CH_3$, 2$CH_2$butyl, 8-$CH_2\underline{CH_3}$), 1.51, 1.49, 1.37 & 1.36 (each singlet for 36H, $CO_2Bu^t$), 1.10 (t, 3H, $CH_3$-Obutyl, J=7.6 Hz), 0.87 (t, 3H, $CH_3$-Nbutyl, J=7.4 Hz), –0.02 (brs, 1H, NH), –0.12 (brs, 1H, NH). EIMS: 1263 ($m^+$).

Compound No. 12

Compound 11 (60.0 mg) was stirred in 5 ml of 70% TFA/DCM for 3 hr at room temperature. Reaction mixture was concentrated and dried under high vacuum to give 12 in quantitative yield.

Yield: 42.0 mg (85.19%). UV-vis (λmax $cm^{-1}$, dichloromethane): 363, 415, 508, 547 & 701. EIMS: 1039 ($m^+$).

In Vivo Photosensitizing Efficacy

The experiments were performed in female BALB/c mice (6-8 weeks of age) purchased from Clarence Reeder (National Cancer Institute Fredrick Cancer Research Facility, Fredrick, Md.). The mice were injected s.c. in the axilla with $10^6$ Colo-26 cells in 50 μL complete RPMI-1640 and were used for experimentation when the tumors reached 5-6 mm. All experiments were performed under the approved protocols of the RPCI Animal Care and Use Committee and followed DLAR regulations.

(a) Comparative Photosensitizing Efficacy of 15 vs its water soluble analog 16:

BALB/c mice inoculated with Colon-26 tumors were injected with 0.7λmoles/kg of either PS 15 or 16 and at ~24 h p.i., the mice were treated with PDT for a total fluence of 135 J/cm² at 75 mW/cm² (30 minute treatment). Preliminary studies had shown that PS 15 was only 30% effective using the 135 J/cm² at 75 mW/cm² (30 minute) PDT regimen. However, when its water-soluble analog was tested, the PDT response enhanced to 70% mice tumor-free by day 90.

Three explanations for this may be that (1) the slight charge from the carboxylate groups may be contributing to differing localization sites of PS 16 in comparison to 15 (as mentioned above), (2) the PDT-induced mechanism of action may differ in comparison to 16 or (3) the increased PS uptake in the tumor compared to the skin of 16 could be contributing to the enhanced PDT response. The main purpose of these experiments was to determine if the water-soluble PS could be utilized as both a PDT agent and diagnostic imaging tool. The initial in vivo experiments displayed the advantage of the water-soluble PS over its parent compound, 15.

Comparative Photosensitizing Efficacy Water-soluble Photosensitizers 9 and 12

The in vivo photosensitizing efficacy of water-soluble photosensitizers 9 and 12 was determined in BALB-C mice bearing Colo-26 tumors at similar treatment conditions. At 24 h postinjction of the photosensitizer (i. v., 0.5 μmol/Kg), the tumors were exposed to laser light (at the photosensitizer's longest wavelength absorption (135J/cm², 75 mW/cm² for 30 min) and the tumor regrowth was measured daily. The results are summarised in Figure X. As can be seen among the three candidates, compared to 12, compounds 9 and 12 were found to be more effective.

In Vivo Fluorescence Imaging With the Water-Soluble Analog 16

Measurement of PS accumulation in the tumor and skin via fluorescence measurements using a non-invasive optical imaging camera system was performed. When tumors reached 4-5 mm in diameter, the BALB/c mice were imaged prior to PS injection (using body weight of Ketamine Xylazine or 80 mg/kg of Pentobarbital Sodium anesthesia) to make certain that no endogenous chromophores were excited at the particular wavelengths utilized (425/50 nm or 540/40 nm excitation filters). Background fluorescence measurements had been a concern for previous researchers because it was found that the current diet of the mice contained chlorophyll ($\lambda_{max}$ fluorescence=676 nm). When evaluating a photosensitizer such as HPPH, the PS emission peak at ~668 nm overlapped with that of chlorophyll. Therefore, the fluorescence images obtained were not particularly specific for only PS fluorescence. For instance, when the background mice were imaged (No PS) using an excitation wavelength of 425/50 nm the chlorophyll from the diet was present in both the hair (yellow) and BALB/c skin (red) exhibiting an emission peak at ~676 nm. For the experiments with PS 15 and 16, there was no concern that the emission peak of chlorophyll would overlap with that of the PS (emission at ~710 nm).

For non-invasive in vivo imaging of PS fluorescence, the Nuance™ Imaging Camera was beneficial in that once anesthetized the whole body of the mouse could be placed into the imaging LT-9CABINET, which provided the proper light insulation required for measurement and the ILLUMATOOL low power light source necessary for keeping the amount of light delivered to each mouse constant (3 mice per time point). This imaging technology was quite beneficial due to the fact that it was minimally invasive, so that there was no need to sacrifice the animal in order to obtain information about where the PS was localized. Previous studies have involved invasive procedures in which a mouse was sacrificed, the tumor or skin was excised and histological staining was performed on the paraffin blocks. Below are fluorescence images of PS 16 excited using the 425/50 nm filter and collected via the non-invasive CCD Nuance Imaging Camera (Princeton Instruments Inc.). This system was capable of taking qualitative hyperspectral images in the specific range of 650-720 nm focused on 710 nm. Attached to the small animal images are the spectral properties of the hair (yellow), skin (blue) and tumor (red).

Figure 3:
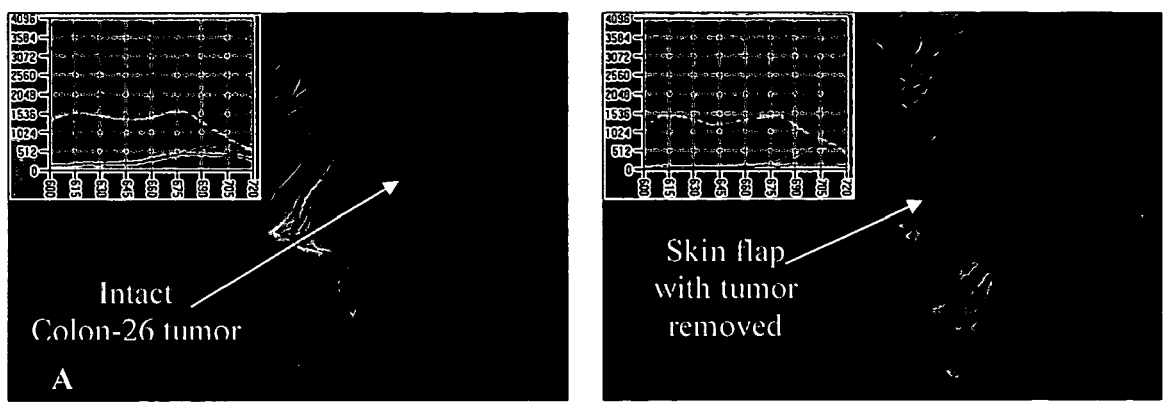
FIG. 3 shows an In vivo fluorescence image of PS 16 (24 h p.i.). A: intact tumor; B: skin flap with tumor removed so that PS fluorescence could be imaged on underside.
Figure 3A:
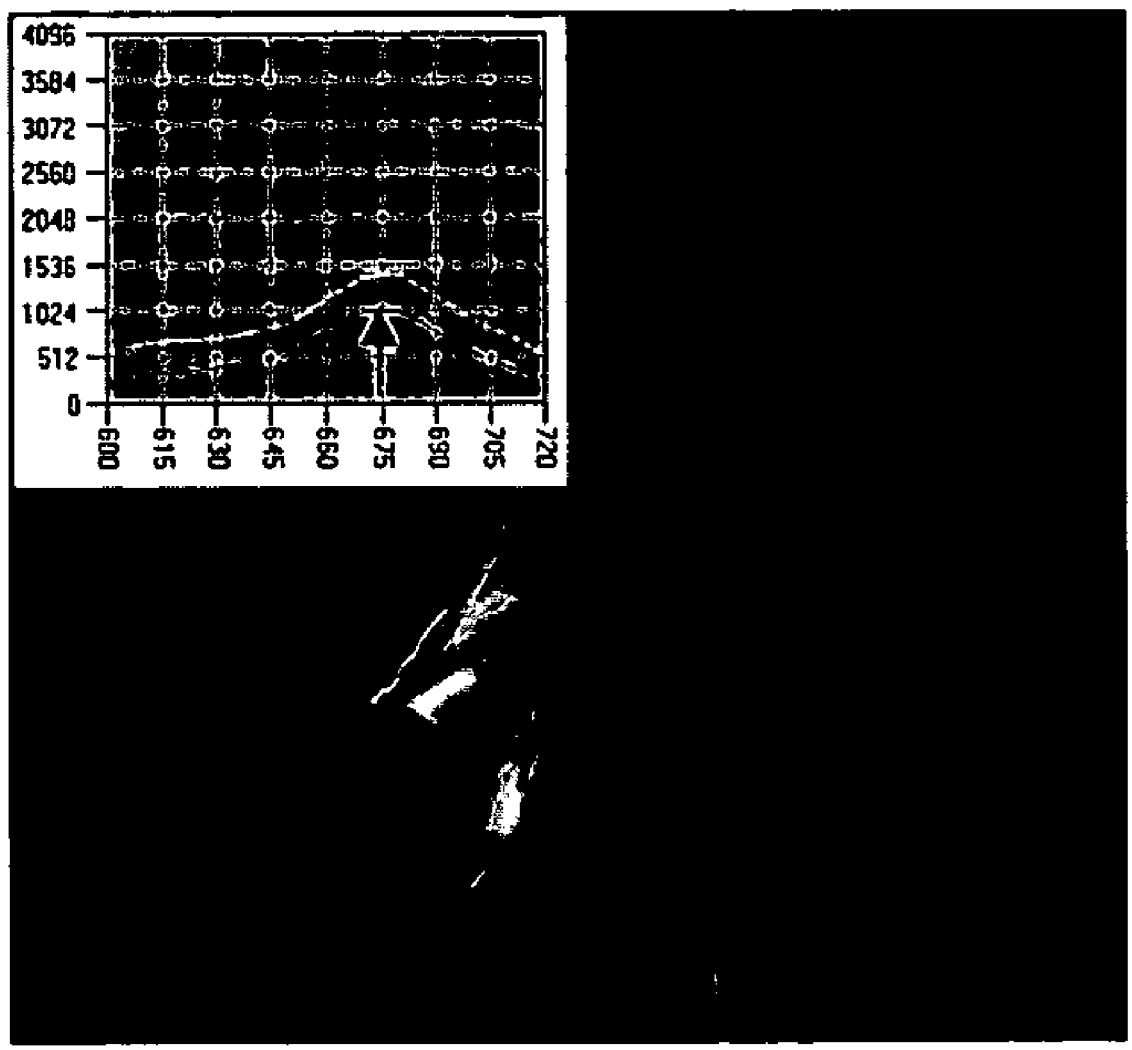
FIG. 3A shows a BALB/c Colon-26 background fluorescence image prior to PS injection.
Figure 4:
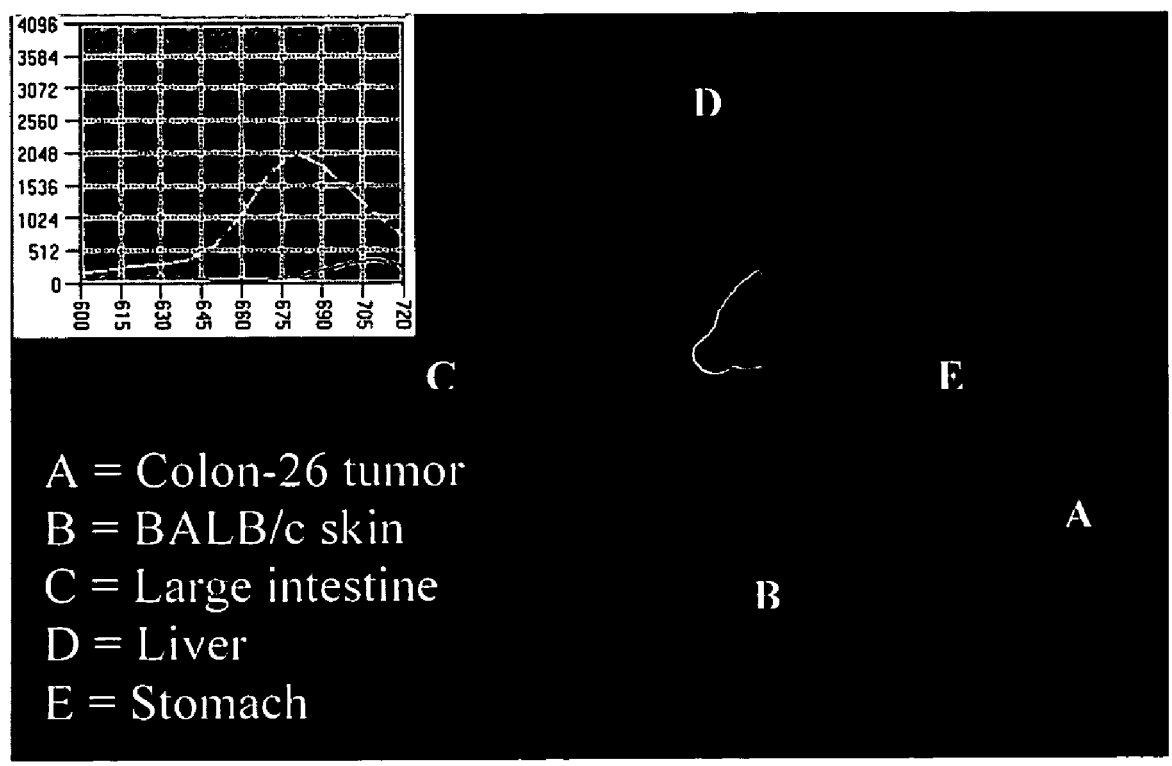
FIG. 4 shows an In vivo fluorescence image of PS 16 in various organs (24 h p.i.). A: Colon-26 tumor; B: skin over tumor; C: large intestine; D: liver; E: stomach.

From FIG. 3, it can be seen that PS 16 showed a significant selectivity for tumors (peak fluorescence at ~710 nm), but when the skin flap was performed there appeared to be a noticeable amount of PS remaining in the underside of the skin after tumor removal. It is important to remember that these are qualitative images of PS accumulation in the tumor and skin. As a means to determine the exact uptake of the PS in the tumor versus the skin and other organs, a skin-flap excision, as well as, an ex vivo biodistribution study were performed. Once removed, the organs (tumor, skin, heart, spleen, muscle, kidney, stomach, intestine, lung and liver) were placed on a plexiglass plate and their fluorescence was collected (425/50 nm excitation). The fluorescence image displayed fluorescence peaks at ~675 (yellow spectrum characteristic of chlorophyll-a from diet) and ~710 nm (red spectrum characteristic of PS 16) with visible fluorescence in the tumor, skin, large intestine, liver and stomach. The organs were homogenized, dissolved in Solvable and read on the Fluoromax II Fluorimeter at 417 nm. After reading the fluorescence of all the organ samples, it was determined that the tumor and liver retained PS 16 (peak emission ~710 nm), while the skin, stomach and intestine retained material characteristic of chlorophyll-a (peak emission 676 nm). The average fluorescence per mg/mL of protein was normalized to background mice (no PS) and plotted for each organ (avg. of 3 samples per organ).

This invention describes the successful synthesis of a new long wavelength water-soluble PS. The in vitro and in vivo PDT photosensitizing experiments indicated that PS 16 was superior to its parent compound, 15

At its therapeutic PDT dose of 0.7 μmoles/kg (70% mice were tumor-free by day 60, 7/10 mice), PS 16 displayed selective tumor uptake at 24 h p.i. as visualized by Nuance™ imaging and confirmed by the fluorescence extraction experiments. This is the first report of a water-soluble fluorinated purpurinimide being utilized as a dual PDT-imaging agent.

What is claimed is:

1. A tetrapyrollic photosensitizer compound having at least one pendant —$CH_2CH_2CON(CH_2CON(CH_2COOH)_2)_2$ or —$N(CH_2COOH)_2$ group or esters thereof said tetrapyrollic compound being a chlorin, bacteriochlorin, porphyrin, pyropheophorbide, purpurinimide, or bacteriopurpurinimide.

2. A compound of the formula:

[chemical structure showing macrocycle with positions labeled $R_1$, $R_{1a}$, $R_2$, $R_{2a}$, $R_3$, $R_{3a}$, $R_4$, $R_{4a}$, $R_5$, $R_6$, $R_{6a}$, $R_7$, $R_8$, $R_{8a}$, $R_9$, $R_{10}$ with rings a, b, c, d and NH, N, H, HN]

or a phamaceutically acceptable derivative thereof, wherein:
  $R_1$ and $R_2$ are each independently substituted or unsubstituted alkyl, substituted or unsubstituted alkenyl, —C(O)$R_a$ or —COOR$_a$ or —CH(CH$_3$)(OR) or —CH(CH$_3$)(O(CH$_2$)$_n$XR) where $R_a$ is hydrogen, substituted or unsubstituted alkyl, substituted or unsubstituted alkenyl, substituted or unsubstituted alkynyl, or substituted or unsubstituted cycloalkyl where $R_2$ may be CH=CH$_2$, CH(OR$_{20}$)CH$_3$, C(O)Me, C(=NR$_{21}$)CH$_3$ or CH(NHR$_{21}$)CH$_3$;
  where X is an aryl or heteroaryl group;
  n is an integer of 0 to 6;
  R and R' are independently H or lower alkyl of 1 through 8 carbon atoms;
  where $R_{20}$ is methyl, butyl, heptyl, docecyl or 3,5-bis(trifluoromethyl)-benzyl; and
  $R_{21}$ is 3,5,-bis(trifluoromethyl)benzyl;
  $R_{1a}$ and $R_{2a}$ are each independently hydrogen or substituted or unsubstituted alkyl, or together form a covalent bond;
  $R_3$ and $R_4$ are each independently hydrogen or substituted or unsubstituted alkyl;
  $R_{3a}$ and $R_{4a}$ are each independently hydrogen or substituted or unsubstituted alkyl, or together form a covalent bond;
  $R_5$ is hydrogen or substituted or unsubstituted alkyl;
  $R_6$ and $R_{6a}$ are each independently hydrogen or substituted or unsubstituted alkyl, or together form =O;
  $R_7$ is a covalent bond, alkylene, azaalkyl, or azaaraalkyl or =NR$_{20}$ where $R_{20}$ is hydrogen or lower alkyl of 1 through 8 carbon atoms or —CH$_2$-3,5-bis(tri-fluoromethyl)benzyl or —CH$_2$X-R$^1$ or —YR$^1$ where Y is an aryl or heteroaryl group;
  $R_8$ and $R_{8a}$ are each independently hydrogen or substituted or unsubstituted alkyl or together form =O;
  $R_9$ is —CH$_2$CH$_2$CON(CH$_2$CON(CH$_2$COOH)$_2$)$_2$; or —N(CH$_2$COOH)$_2$
  $R_{10}$ is hydrogen, or substituted or unsubstituted alkyl and;
  each of $R_1$-$R_{10}$, when substituted, is substituted with one or more substituents each independently selected from Q, where Q is alkyl, haloalkyl, halo, pseudohalo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue;
  each Q is independently unsubstituted or is substituted with one or more substituents each independently selected from Q$_1$, where Q$_1$ is alkyl, haloalkyl, halo, pseudohalo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue.

3. A compound according to claim 2 having the formula:

[chemical structure of chlorin derivative with Me, Et substituents and hexyloxy chain, with amide linkages to N-substituted diacetic acid groups bearing COOH groups]

4. A compound according to claim 2 having the formula:

[chemical structure of chlorin derivative similar to claim 3 but with 3,5-bis(trifluoromethyl)benzyl substituent, CF$_3$ groups, and COOH groups]

5. A compound according to claim 2 having the formula:

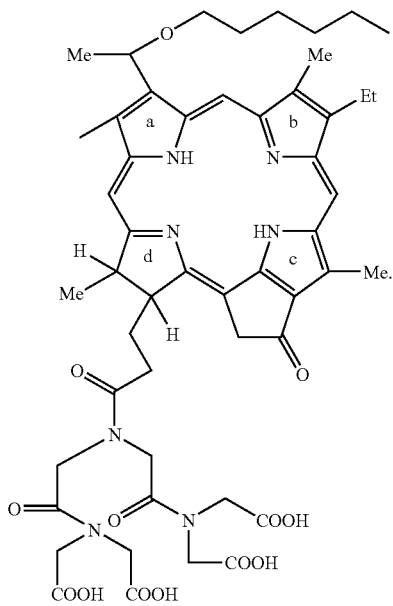

6. The compound of claim 2, wherein:
$R_1$ is substituted or unsubstituted alkyl;
$R_2$ is substituted or unsubstituted alkyl, substituted or unsubstituted alkenyl, or —C(O)$R_a$,
where $R_a$ is substituted or unsubstituted alkyl;
$R_{1a}$ and $R_{2a}$ together form a covalent bond;
$R_3$ and $R_4$ are each independently substituted or unsubstituted alkyl;
$R_{3a}$ and $R_{4a}$ are each independently hydrogen, or together form a covalent bond;
$R_5$ is substituted or unsubstituted alkyl;
$R_6$ and $R_{6a}$ together form =O;
$R_7$ is azaalkyl, or azaaralkyl;
$R_8$ and $R_{8a}$ together form =O;
$R_9$ and $R_{10}$ are each independently substituted or unsubstituted alkyl;
each of $R_1$-$R_{10}$, when substituted, is substituted with one or more substituents each independently selected from Q, where Q is halo, pseudohalo, haloalkyl, COOR$_b$ where R$_b$ is hydrogen or alkyl, OR$_c$ where R$_c$ is alkyl or aralkyl, NR$_f$R$_g$ where R$_f$ and R$_g$ are each independently hydrogen, alkyl or aralkyl, or =NR$_h$ where R$_h$ is aralkyl;
each Q is independently unsubstituted or is substituted with one or more substituents each independently selected from $Q_1$, where $Q_1$ is halo, pseudohalo, or haloalkyl.

7. The compound of claim 2, wherein:
$R_1$ is unsubstituted alkyl;
$R_2$ is substituted or unsubstituted alkyl, unsubstituted alkenyl, or —C(O)$R_a$, where $R_a$ is unsubstituted alkyl;
$R_{1a}$ and $R_{2a}$ together form a covalent bond;
$R_3$ and $R_4$ are each independently unsubstituted alkyl;
$R_{3a}$ and $R_{4a}$ are each independently hydrogen, or together form a covalent bond;
$R_5$ is unsubstituted alkyl;
$R_6$ and $R_{6a}$ together form =O;
$R_7$ is azaalkyl, or azaaralkyl;
$R_8$ and $R_{8a}$ together form =O;
$R_{10}$ is unsubstituted alkyl;
each of $R_1$-$R_{10}$, when substituted, is substituted with one or more substituents each independently selected from Q, where Q is halo, pseudohalo, haloalkyl, COOR$_b$ where R$_b$ is hydrogen or alkyl, OR$_c$ where R$_c$ is alkyl or aralkyl, NR$_f$R$_g$ where R$_f$ and R$_g$ are each independently hydrogen, alkyl or aralkyl, or =NR$_h$ where R$_h$ is aralkyl;
each Q is independently unsubstituted or is substituted with one or more substituents each independently selected from $Q_1$, where $Q_1$ is halo, pseudohalo, or haloalkyl.

8. The compound of claim 2, wherein:
$R_1$ is methyl;
$R_{1a}$ and $R_{2a}$ together form a covalent bond;
$R_3$ is methyl;
$R_4$ is ethyl;
$R_{3a}$ and $R_{4a}$ are each independently hydrogen, or together form a covalent bond;
$R_5$ is methyl; and
$R_{10}$ is methyl.

9. The compound claim 2, wherein:
$R_2$ is CH=CH$_2$, CH(OR$_{20}$)CH$_3$, C(O)Me, C(=NR$_{21}$)CH$_3$ or CH(NHR$_{21}$)CH$_3$;
where $R_{20}$ is methyl, butyl, heptyl, dodecyl or 3,5-bis(trifluoromethyl)-benzyl; and
$R_{21}$ is 3,5-bis(trifluoromethyl)benzyl.

10. The compound of claim 2, wherein:
$R_7$ is =NR$_{20}$, where $R_{20}$ is methyl, butyl, heptyl, dodecyl or 3,5-bis(trifluoromethyl)-benzyl.

11. A pharmaceutical composition, comprising a compound of claim 1 or a pharmaceutically acceptable derivative thereof in a pharmaceutically acceptable carrier.

12. A pharmaceutical composition, comprising a compound of claim 2 or a pharmaceutically acceptable derivative thereof in a pharmaceutically acceptable carrier.

* * * * *